(12) United States Patent
Wang et al.

(10) Patent No.: US 7,396,830 B2
(45) Date of Patent: Jul. 8, 2008

(54) PIPERAZINE AMIDINES AS ANTIVIRAL AGENTS

(75) Inventors: Tao Wang, Farmington, CT (US); John F. Kadow, Wallingford, CT (US); Nicholas A. Meanwell, East Hampton, CT (US); Zhongxing Zhang, Madison, CT (US); Zhiwei Yin, Glastonbury, CT (US); Clint A. James, Longueuil (CA); Edward H. Ruediger, Greenfield Park (CA); Bradley C. Pearce, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/541,826

(22) Filed: Oct. 2, 2006

(65) Prior Publication Data

US 2007/0078141 A1    Apr. 5, 2007

Related U.S. Application Data

(60) Provisional application No. 60/723,580, filed on Oct. 4, 2005.

(51) Int. Cl.
*A61K 31/496*    (2006.01)
*C07D 209/20*    (2006.01)
*C07D 417/04*    (2006.01)
*C07D 471/04*    (2006.01)

(52) U.S. Cl. ............ 514/234.5; 514/235.2; 514/252.11; 514/253.04; 514/253.09; 514/254.02; 514/254.09; 544/121; 544/295; 544/357; 544/362; 544/373; 544/369

(58) Field of Classification Search ..................... None
See application file for complete search history.

(56) References Cited

OTHER PUBLICATIONS

Drug Evaluations by American Medical Association (6$^{th}$ Ed.), pp. 1615-1627 (1986).*

* cited by examiner

*Primary Examiner*—Emily Bernhardt

(57) ABSTRACT

This disclosure provides compounds of Formula I

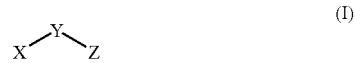

as described herein having drug and bio-affecting properties, their pharmaceutical compositions and method of use. In particular, the disclosure is concerned with indole and azaindole piperazine diamide derivatives that possess unique antiviral activity. More particularly, the present disclosure relates to compounds useful for the treatment of HIV and AIDS.

6 Claims, No Drawings

PIPERAZINE AMIDINES AS ANTIVIRAL AGENTS

CROSS-REFERENCE TO RELATED APPLICATIONS

This application claims the benefit of U.S. Provisional Application Ser. No. 60/723,580 filed Oct. 4, 2005.

FIELD OF THE DISCLOSURE

This disclosure provides compounds having drug and bio-affecting properties, their pharmaceutical compositions and method of use. In particular, the disclosure is concerned with indole and azaindole piperazine diamide derivatives that possess unique antiviral activity. More particularly, the present disclosure relates to compounds useful for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), emtricitabine (or FTC), Combivir® (contains –3TC plus AZT), Trizivir® (contains abacavir, lamivudine, and zidovudine), Epzicom® (contains abacavir and lamivudine), Truvada® (contains Viread® and emtricitabine); non-nucleoside reverse transcriptase inhibitors: nevirapine (or Viramune®), delavirdine (or Rescriptor®) and efavirenz (or Sustiva®), and peptidomimetic protease inhibitors or approved formulations: saquinavir, indinavir, ritonavir, nelfinavir, amprenavir, lopinavir, and Kaletra®(lopinavir and Ritonavir). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents currently being studied by a number of investigators.

The properties of a class of HIV entry inhibitors called HIV attachment inhibitors has been improved in an effort to obtain compounds with maximized utility and efficacy as antiviral agents. A disclosure describing indoles of which the structure shown below for BMS-705 is representative has been disclosed [Antiviral Indoleoxoacetyl Piperazine Derivatives. Wade Blair; Millind Deshpande; Haiquan Fang; Ping-Fang Lin; Tim Spencer; Owen Wallace; Hui Wang; Tao Wang; Zhongxing Zhang and Kap-Sun Yeung WO-00076521 (U.S. Pat. No. 6,469,006 issued), 2000].

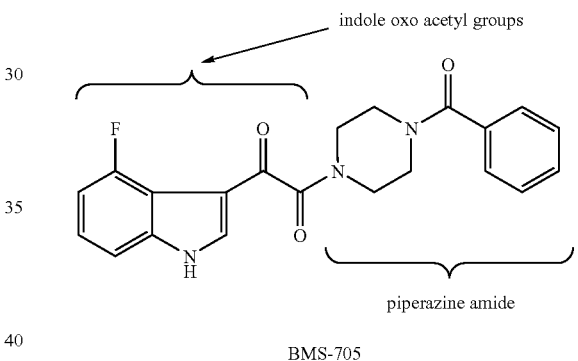

BMS-705

Two other compounds, referred to in the literature as BMS-806 and BMS-043 have been described in both the academic and patent art:

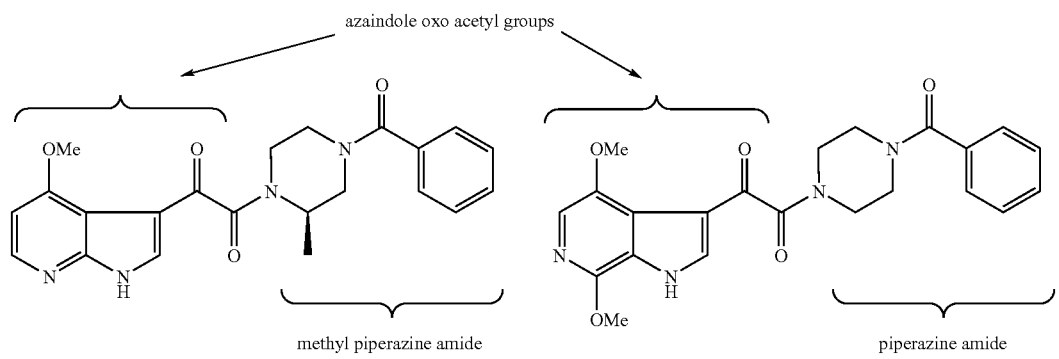

BMS-806      BMS-043

(1) A small molecule HIV-1 inhibitor that targets the HIV-1 envelope and inhibits CD4 receptor binding (Lin, Pin- Fang; Blair, Wade; Wang, Tao; Spicer, Timothy; Guo, Qi; Zhou, Nannan; Gong, Yi-Fei; Wang, H.-G. Heidi; Rose, Ronald; Yamanaka, Gregory; Robinson, Brett; Li, Chang-Ben; Fridell, Robert; Deminie, Carol; Demers, Gwendeline; Yang, Zheng; Zadjura, Lisa; Meanwell, Nicholas; and Colonno, Richard. Proceedings of the National Academy of Sciences of the United States of America (2003), 100(19), 11013-11018);

(2) Biochemical and genetic characterizations of a novel human immunodeficiency virus type 1 inhibitor that blocks gp120-CD4 interactions (Guo, Qi; Ho, Hsu-Tso; Dicker, Ira; Fan, Li; Zhou, Nannan; Friborg, Jacques; Wang, Tao; McAuliffe, Brian V.; Wang, Hwei-gene Heidi; Rose, Ronald E.; Fang, Hua; Scarnati, Helen T.; Langley, David R.; Meanwell, Nicholas A.; Abraham, Ralph; Colonno, Richard J.; and Lin, Pin-fang. Journal of Virology (2003), 77(19), 10528-10536);

(3) Method using small heterocyclic compounds for treating HIV infection by preventing interaction of CD4 and gp120 (Ho, Hsu-Tso; Dalterio, Richard A.; Guo, Qi; and Lin, Pin-Fang. PCT Int. Appl. (2003), WO 2003072028 A2);

(4) Antiviral Azaindole Derivatives Useful for the Treatment of HIV Infection (Wang, Tao; Wallace, Owen; Zhang, Zhongxing; Meanwell, Nicolas A.; and Bender, John A. WO-00162255 (corresponding to U.S. Pat. Nos. 6,476,034 and 6,900,323), 2001);

(5) Method using small heterocyclic compounds for treating HIV infection by preventing interaction of CD4 and gp120. (Ho, Hsu-Tso; Dalterio, Richard A.; Guo, Qi; and Lin, Pin-Fang. PCT Int. Appl. (2003), WO 2003072028A2); and (6) Discovery of 4-benzoyl-1-[(4-methoxy-1H-pyrrolo[2, 3-b]pyridin-3-yl)oxoacetyl]-2-(R)-methylpiperazine (BMS-378806): A Novel HIV-1 Attachment Inhibitor That Interferes with CD4-gp120 Interactions. (Wang, Tao; Zhang, Zhongxing; Wallace, Owen B.; Deshpande, Milind; Fang, Haiquan; Yang, Zheng; Zadjura, Lisa M.; Tweedie, Donald L.; Huang, Stella; Zhao, Fang; Ranadive, Sunanda; Robinson, Brett S.; Gong, Yi-Fei; Ricarrdi, Keith; Spicer, Timothy P.; Deminie, Carol; Rose, Ronald; Wang, Hwei-Gene Heidi; Blair, Wade S.; Shi, Pei-Yong; Lin, Pin-fang; Colonno, Richard J.; and Meanwell, Nicholas A. Journal of Medicinal Chemistry (2003), 46(20), 4236-4239).

Some description of their properties in human clinical trials have been disclosed ("Antiviral Activity, Safety, and Tolerability of a Novel, Oral Small-Molecule HIV-1 Attachment Inhibitor, IVa, in HIV-1-Infected Subjects" G. Hanna, J. Lalezari, J. Hellinger, D. Wohl, T. Masterson, W. Fiske, J. Kadow, P-F. Lin, M. Giordano, R. Colonno, D. Grasela. Abstract J-32, Feb. 11, 2004, 11th Conference on Retroviruses and Opportunistic Infections (CROI), San Francisco, Calif.).

It should be noted that in all three of these structures, a piperazine amide (In these three structures a piperazine phenyl amide) is present and this group is directly attached to an oxoacetyl moiety. The oxoacetyl group is attached at the 3-position of 4-Fluoro indole in BMS-705 and to the 3 position of substituted azaindoles in BMS-806 and BMS-043.

In an effort to obtain improved anti-HIV compounds, later publications described in part, modifed substitution patterns on the indoles and azaindoles:

(1) Novel Substituted Indoleoxoacetic Piperazine Derivatives Useful for treating HIV Infection and AIDS. (Wallace, Owen B.; Wang, Tao; Yang, Kap-Sun; Pearce, Bradley; Meanwell, Nicholas A.; Qiu, Zhilei; Fang, Haiquan; Xue, Qiufen May and Yin, Zhiwei. WO-00204440 (corresponding to U.S. Pat. No. 6,573, 262 & U.S. Pat. No. 6,632,819));

(2) Preparation and antiviral activity of substituted piperazinyloxoacetylindole derivatives. (Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. U.S. Pat. Appl. Publ. 2003069245);

(3) Composition and Antiviral Activity of Substituted Azaindoleoxoacetic Piperazine Derivatives. (Wang, Tao; Zhang, Zhongxing; Meanwell, Nicholas A.; Kadow, John F.; and Yin, Zhiwei. WO-02062423);

(4) Composition and antiviral activity of substituted azaindoleoxoacetic piperazine derivatives. (Wang, Tao; Zhang, Zhongxing; Meanwell, Nicholas A.; Kadow, John F.; Yin, Zhiwei; and Xue, Qiufen May. U.S. Pat. Appl. Publ. 20030207910); and (5) Composition and antiviral activity of substituted azaindoleoxoacetic piperazine derivatives. (Wang, Tao; Zhang, Zhongxing; Meanwell, Nicholas A.; Kadow, John F.; Yin, Zhiwei; Xue, Qiufen May; Regueiro-Ren, Alicia; Matiskella, John D.; Ueda, Yasutsugu. U.S. Pat. Appl. Publ. 2004110785).

Replacement of these groups with other heteraromatics or substituted heteroaroamatics or bicyclic hydrocarbons was also shown to be feasible:

(1) Indole, Azaindole and Related Heterocyclic Amidopiperazine Derivatives. Wang, Tao; Wallace, Owen B.; Meanwell, Nicholas A.; Zhang, Zhongxing; Bender, John A.; and Kadow, John F. WO-02085301 (corresponding to U.S. Pat. No. 6,825,201);

(2) Bicyclo 4.4.0 Antiviral Derivatives. (Wang, Tao; Wallace, Owen B.; Meanwell, Nicholas A.; Kadow, John F.; Zhang, Zhongxing; and Yang, Zhong. WO-03092695); and (3) A preparation of diazaindole derivatives, useful as antiviral agents. (Bender, John A.; Yang, Zhong; Kadow, John F.; and Meanwell, Nicholas A. US2005124623).

A select few replacements for the piperazine amide portion of the molecules have also been described in the art and among these examples are (A) Piperidine Alkenes:

(1) Indole, Azaindole and Related Heterocyclic 4-Alkenyl Piperidine Amides. (Wang, Tao; Kadow, John F.; Meanwell, Nicholas A.; Zhang, Zhongxing; Yin, Zhiwei; Yeung, Kap-Sun; Qiu, Zhilei; Deon, Daniel H.; James, Clint A.; Ruedinger, Edward H., and Bachand, Carol. US-2004/0063744); and (2) Preparation and pharmaceutical compositions of indole, azaindole and related heterocyclic 4-alkenyl piperidine amides. (Wang, Tao; Kadow, John F.; Meanwell, Nicholas A.; Yeung, Kap-Sun; Zhang, Zhongxing; Yin, Zhiwei; Qiu, Zhilei; Deon, Daniel H.; James, Clint A.; Ruediger, Edward H.; and Bachand, Carol. U.S. Pat. Appl. 2004/0186292).

(B) Certain Pyrrolidine Amides:

Indole, Azaindole and Related Heterocyclic Pyrrolidine Derivatives. (Kadow, John F.; Xu, Qiufen; Wang, Tao; Zhang, Zhongxing; and Meanwell, Nicholas A. WO-03068221, 2003.);

(C) N-aryl or Heteroaryl Piperazines:

Preparation of (aza)indolyloxoacetylpiperazines as anti-HIV drugs (Yeung, Kap-Sun; Farkas, Michelle; Kadow, John F.; Meanwell, Nicholas A.; Taylor, Malcolm; Johnston, David; Coulter, Thomas Stephen; Wright, J. J. Kim. WO-2005004801, 2005.);

(D) Piperazinyl Ureas:
(1) Preparation of indolyl-, azaindolyl-, and related heterocyclic sulfonylureidopiperazines for treatment of HIV and AIDS. (Kadow, John F.; Regueiro-Ren, Alicia; Xue, Qiufen May. WO-2004000210, 2003); and
(2) Preparation of indolyl-, azaindolyl-, and related heterocyclic ureido and thioureido piperazines for treatment of HIV and AIDS. (Regueiro-Ren, Alicia; Xue, Qiufen May; Kadow, John F.; and Taylor, Malcolm. WO-2004011425, 2004).

A method for preparing prodrugs was also disclosed in this class (Prodrugs of Piperazine and Substituted Piperidine Antiviral Agents. (Ueda et al., U.S. non-provisional application Ser. No. 11/066,745, filed Feb. 25, 2005).

A publication on new compounds in this class of attachment inhibitors (Jinsong Wang et. al. Org. Biol. Chem. 2005, 3, 1781-1786.) and a patent application on some more remotely related compounds have appeared WO2005/016344 published on Feb. 24, 2005.

Nothing in these references can be construed to disclose or suggest the novel compounds of-this disclosure and their use to inhibit HIV infection.

SUMMARY OF THE DISCLOSURE

The present disclosure relates to compounds of Formula I, their pharmaceutical formulations, and their use in patients suffering from or susceptible to a virus such as HIV. The compounds of Formula I, which include pharmaceutically acceptable salts and/or solvates (e.g., hydrates) thereof, have the formula and meaning as described below. Are effective antiviral agents, particularly as inhibitors of HIV.

A first embodiment of the present disclosure relates to compounds of Formula I, including pharmaceutically acceptable salts thereof,

(I)

wherein:
X is selected from the group consisting of:

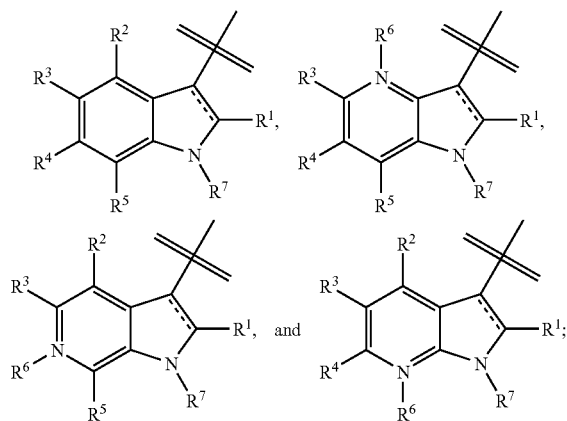

$R^1$ is H;
$R^2$ is halogen or $C_1$-$C_3$ alkoxy;
$R^3$ and $R^4$ are independently H or halogen;
$R^5$ is selected from the group consisting of hydrogen, halogen, methoxy, and B;
$R^6$ is O or does not exist;
═ represents a carbon-carbon bond;
B is selected from the group consisting of $C(O)NR^{14}R^{15}$, phenyl and heteroaryl; wherein said phenyl and heteroaryl are independently optionally substituted with one to three same or different halogens or from one to three same or different substituents selected from F defined below; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;
F is selected from the group consisting of $(C_{1-6})$alkyl, phenyl, and —$CONR^{16}R^{17}$; wherein said phenyl is optionally substituted with one to three same or different halogens or one to three methyl groups or cyano;
$R^{14}$ and $R^{15}$ are independently hydrogen or $(C_{1-6})$alkyl;
$R^{16}$ and $R^{17}$ are independently hydrogen or $(C_{1-6})$alkyl;

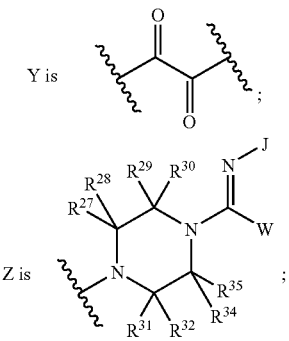

J is selected from the group consisting of hydrogen, $(C_{1-6})$alkyl, phenyl, pyridyl, $(C_{3-6})$cycloalkyl, $C(═O)NR^{18}R^{19}$, $C(═O)OR^{20}$, $C(═O)R^{21}$, cyano, and $SO_2G^3$, wherein said $(C_{1-6})$alkyl, may be optionally substituted with one to three same or different members selected from the group J-1;
$R^{18}$ and $R^{19}$ are each independently H, $(C_{1-6})$alkyl, or phenyl;
$R^{20}$ and $R^{21}$ are each independently $(C_{1-6})$alkyl;
$G^3$ is selected from the group consisting of $(C_{1-6})$alkyl, $(C_{3-6})$cycloalkyl, $N((C_{1-6}alkyl)_2$, and phenyl;
J-1 is selected from the group consisting of —$NR^{35}R^{36}$, morpholino, piperazinyl, ester, hydroxy, alkyloxy, and N-Me piperazinyl;
W is phenyl or pyridinyl;
$R^{27}$, $R^{28}$, $R^{29}$, $R^{30}$, $R^{31}$, $R^{32}$, $R^{34}$ and $R^{35}$ are independently selected from the group consisting of hydrogen, or one or two $(C_{1-6})$alkyl optionally substituted with 1 to 3 fluorines.

In a specific embodiment, J is methyl, CN or hydrogen.

Another embodiment of the present disclosure is a method for treating mammals infected with a virus, especially wherein said virus is HIV, comprising administering to said mammal an antiviral effective amount of a compound of Formula I, and one or more pharmaceutically acceptable carriers, excipients or diluents. Optionally, the compound of Formula I can be administered in combination with an antiviral effective amount of an AIDS treatment agent selected from the group consisting of: (a) an AIDS antiviral agent; (b) an anti-infective agent; (c) an immunomodulator; and (d) HIV entry inhibitors.

Another embodiment of the present disclosure is a pharmaceutical composition comprising an antiviral effective amount of a compound of Formula I and one or more pharmaceutically acceptable carriers, excipients, diluents and optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION

Continued efforts to search for compounds with improved anti-HIV capabilities have led to the discovery that piperazine amidines can be substituted onto the substituted azaindole oxoacetyl or indole oxoacetyl moieties to provide useful antiviral compounds of this disclosure as depicted by the general formula shown below.

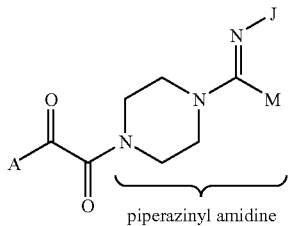

piperazinyl amidine

The inventors of the present disclosures have investigated the utility of the piperidine amidines in combination with other groups that have previously been used to replace the indoles and azaindoles in previous piperazine benzamide work. Compounds with useful antiviral properties have been obtained.

Since the compounds of the present disclosure may possess asymmetric centers, the present disclosure includes the individual diastereoisomeric and enantiomeric forms of the compounds of Formula I in addition to the mixtures thereof.

Definitions

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic(i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$ — groups with Z as defined above.

A "trihalomethanesulfonamido" group refers to a $Z_3CS$(=O)$_2NR^x$— group with Z as defined above and $R^x$ being H or ($C_{1-6}$)alkyl.

A "sulfinyl" group refers to a —S(=O)—R" group, with R" being ($C_{1-6}$)alkyl.

A "sulfonyl" group refers to a —S(=O)$_2$R" group with R" being ($C_{1-6}$)alkyl.

A "S-sulfonamido" group refers to a —S(=O)$_2NR^XR^Y$, with $R^X$ and $R^Y$ independently being H or ($C_{1-6}$)alkyl.

A "N-Sulfonamido" group refers to a R"S(=O)$_2NR_x$— group, with $R_x$ being H or ($C_{1-6}$)alkyl;

A "O-carbamyl" group refers to a —OC(=O)$NR^XR^Y$ group, with $R^X$ and $R^Y$ independently being H or ($C_{1-6}$)alkyl.

A "N-carbamyl" group refers to a $R^xOC$(=O)$NR^y$ group, with $R^x$ and $R^y$ independently being H or ($C_{1-6}$)alkyl.

A "O-thiocarbamyl" group refers to a —OC(=S)$NR^xR^y$ group, with $R^x$ and $R^y$ independently being H or ($C^{1-6}$)alkyl.

A "N-thiocarbamyl" group refers to a $R^xOC$(=S)$NR^y$— group, with $R^x$ and $R^y$ independently being H or ($C_{1-6}$)alkyl.

An "amino" group refers to an —$NH_2$ group.

A "C-amido" group refers to a —C(=O)$NR^xR^y$ group, with $R^x$ and $R^y$ independently being H or ($C_{1-6}$)alkyl.

A "C-thioamido" group refers to a —C(=S)$NR^xR^y$ group, with $R^x$ and $R^y$ independently being H or ($C_{1-6}$)alkyl.

A "N-amido" group refers to a $R^xC$(=O)$NR^y$— group, with $R^x$ and $R^y$ independently being H or ($C_{1-6}$)alkyl.

An "ureido" group refers to a —$NR^xC$(=O)$NR^yR^{y2}$ group, with $R^x$, $R^y$, and $R^{y2}$ independently being H or ($C_{1-6}$) alkyl.

A "guanidino" group refers to a —$R^xNC$(=N)$NR^yR^{y2}$ group, with $R^x$, $R^y$, and $R^{y2}$ independently being H or ($C_{1-6}$) alkyl.

A "guanyl" group refers to a $R^xR^yNC$(=N)— group, with $R^x$ and $R^y$ independently being H or ($C_{1-6}$)alkyl.

A "cyano" group refers to a —CN group.

A "silyl" group refers to a —Si(R")$_3$, with R" being ($C_{1-6}$) alkyl or phenyl.

A "phosphonyl" group refers to a P(=O)(OR$^x$)$_2$ with $R^x$ being ($C_{1-6}$)alkyl.

A "hydrazino" group refers to a —$NR^xNR^yR^{y2}$ group, with $R^x$, $R^y$, and $R^{y2}$ independently being H or ($C_{1-6}$)alkyl.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Physiologically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris (hydroxymethyl)-aminomethane), or with bases such as piperidine or morpholine.

In the method of the present disclosure, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |

-continued

| Drug Name | Manufacturer | Indication |
|---|---|---|
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Emtriva ® (Emtricitabine) | Gilead | HIV infection, AIDS, (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| Maraviroc; (UK 427857) | Pfizer | HIV infection AIDs, (CCR5 antagonist, in development) |
| Trizivir ® | GSK | HIV infection AIDs, (three drug combination) |
| PA-457 | Panacos | HIV infection AIDs, (maturation Inhibitor, in development) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 ONO-4128) | GSK/ONO | HIV infection AIDs, (CCR5 antagonist, in development) |
| BMS-707035 | Bristol-Myers Squibb | HIV infection AIDs, (viral integrase Inhibitor) |
| Integrase Inhibitor | Merck | HIV infection AIDs, viral integrase inhibitor in development |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |

-continued

| Drug Name | Manufacturer | Indication |
|---|---|---|
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this invention with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Preferred combinations are simultaneous or alternating treatments of with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present disclosure and other active agents may be administered separately or in conjunction. In addition, the administration of one element may be prior to, concurrent to, or subsequent to the administration of other agent(s).

Abbreviations

The following abbreviations, most of which are conventional abbreviations well known to those skilled in the art, are used throughout the description of the disclosure and the examples. Some of the abbreviations used are as follows:

h=hour(s)
rt=room temperature
mol=mole(s)
mmol=millimole(s)
g=gram(s)

mg=milligram(s)
mL=milliliter(s)
TFA=trifluoroacetic Acid
DCE=1,2-Dichloroethane
$CH_2Cl_2$=dichloromethane
TPAP=tetrapropylammonium perruthenate
THF=tetrahydofuran
DEPBT=3-(diethoxyphosphoryloxy)-1,2,3-benzotriazin-4(3H)-one
DMAP=4-dimethylaminopyridine
P-EDC=polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-diisopropylethylamine
MCPBA=meta-chloroperbenzoic Acid
azaindole=1H-pyrrolo-pyridine
4-azaindole=1H-pyrrolo[3,2-b]pyridine
5-azaindole=1H-pyrrolo[3,2-c]pyridine
6-azaindole=1H-pyrrolo[2,3-c]pyridine
7-azaindole=1H-pyrrolo[2,3-b]pyridine
PMB=4-methoxybenzyl
DDQ=2,3-dichloro-5,6-dicyano-1,4-benzoquinone
OTf=trifluoromethanesulfonoxy
NMM=4-methylmorpholine
PIP—COPh=1-benzoylpiperazine
NaHMDS=sodium hexamethyldisilazide
EDAC=1-(3-dimethylaminopropyl)-3-ethylcarbodiimide
TMS=trimethylsilyl
DCM=dichloromethane
DCE=dichloroethane
MeOH=methanol
THF=tetrahydrofuran
EtOAc=ethyl acetate
LDA=lithium diisopropylamide
TMP—Li=2,2,6,6-tetramethylpiperidinyl lithium
DME=dimethoxyethane
DIBALH=diisobutylaluminum hydride
HOBT=1-hydroxybenzotriazole
CBZ=benzyloxycarbonyl
PCC=pyridinium chlorochromate Chemistry The present disclosure comprises compounds of Formula I, their pharmaceutical formulations, and their use in patients suffering from or susceptible to HIV infection. The compounds of Formula I include pharmaceutically acceptable salts thereof. General procedures to construct compounds of Formula I and intermediates useful for their synthesis are described in the following Schemes.

Preparation of Compounds of Formula I

It should be noted that in many cases reactions are depicted for only one position of an intermediate, such as the C-7 position of indole or azaindole, for example. It is to be understood that such reactions could be used at other positions, such as C-2, C-4, C-5 and C-6 position of indole or azaindole, of the various intermediates. Reaction conditions and methods given in the specific examples are broadly applicable to compounds with other substitution and other transformations in this application.

Preparation of template A-CO—CO—Cl and A-CO—CO—OH has been described in detail in WO-00076521, WO-00162255, WO-00204440, WO-02062423, WO-02085301, WO-03068221 and US-2004/0063744.

Standard conditions such as reacting amine with acyl halide 1 (Scheme 1a) and carboxyl acid 4 (Scheme 1b) can be used to convert the ketone to the desired amide products. Some general references of these methodologies and directions for use are contained in "Comprehensive Organic Transformation" by Richard C. Larock, Wiley-VCH, New York, 1989, 972 (Carboxylic acids to amides), 979 (Acid halides to amides).

Scheme 1a

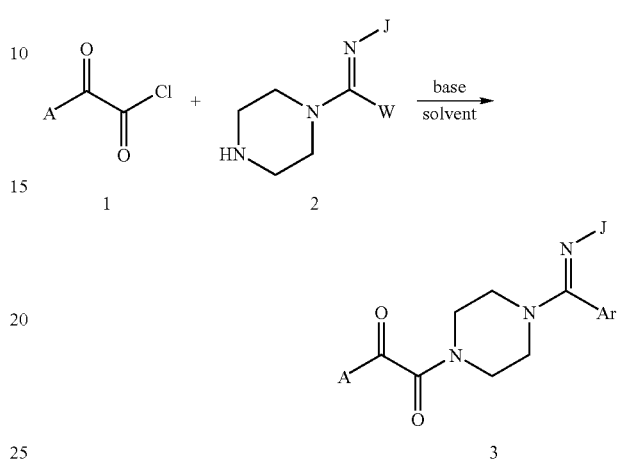

Scheme 1a depicts a general method for forming an amide from piperazine amidine 2 and acyl chloride 1. An appropriate base (from catalytic to an excess amount) selected from sodium hydride, potassium carbonate, triethylamine, DBU, pyridine, DMAP or di-isopropyl ethyl amine was added into a solution of piperazine amidine and acyl chloride in an appropriate solvent selected from dichloromethane, chloroform, benzene, toluene, THF, diethyl ether, dioxane, acetone, N,N-dimethylformamide or pyridine at room temperature. Then reaction was carried out at either room temperature or evaluated temperature up to 150° C. over a period of time (30 minutes to 16 hours) to afford amidine 3, the structure of Formula I. Some selected references involving such reactions include a) *Indian J. Chem., Sect B* 1990, 29, 1077; 2) *Chem. Sci.* 1998, 53, 1216; 3) *Chem. Pharm. Bull.* 1992, 40, 1481; 4) *Chem. Heterocycl. Compd.* 2002, 38, 539.

Scheme 1b

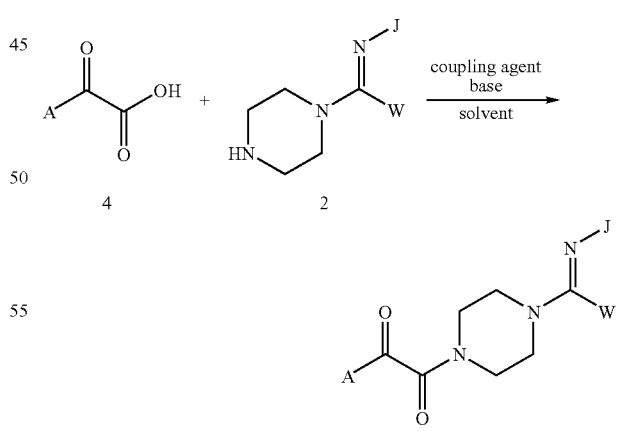

Alternatively, as shown in Scheme 1b, a piperazine amidine 2 can be coupled with an acid 4 using standard amide bond or peptide bond forming coupling reagents. Many reagents for amide bond couplings are known by an organic chemist skilled in the art and nearly all of these are applicable for realizing coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) *J. Chem. Soc. Chem Comm.* 1994, 201; (b) *J. Am. Chem. Soc.* 1994, 116,11580). Additionally, DEPBT (3-(diethoxyphosphoryloxy)-1,2,3-benzotriazin-4(3H)-one) and N,N-diisopropylethylamine, commonly known as Hunig's base, represents another efficient method to form the amide bond and provide compounds of Formula I. DEPBT is either purchased from Adrich or prepared according to the procedure described in *Organic Lett.*, 1999, 1, 91. Typically an inert solvent such as DMF or THF is used but other aprotic solvents could be used.

The piperazine amidines used in Scheme 1a and Scheme 1b may be prepared by methods described in the Schemes 2a -2d.

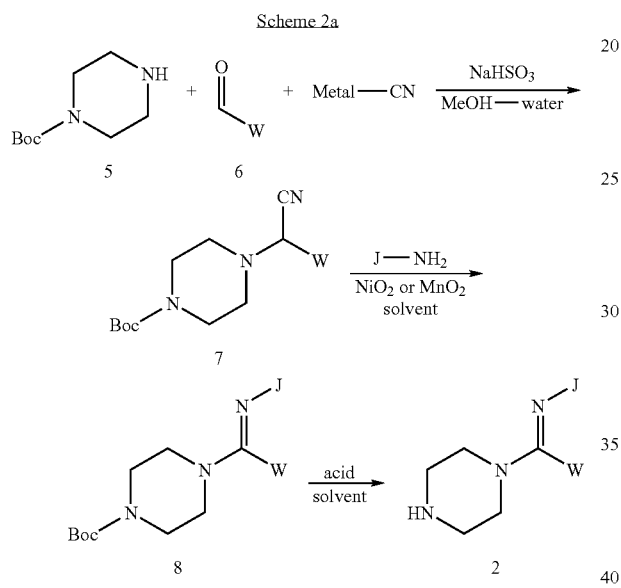

Scheme 2a presents a general route for the preparation of piperazine amidines 2, exemplified in this case by using N-Boc piperazine 5 as the starting material. In a mixed solvent of water and alcohol such as methanol and ethanol, at a temperature between −78° C. and 50° with ambient temperature being preferred, in the absence NaCN or KCN and NaHSO$_3$, N-Boc piperazine 5 can react with an aldehyde 6 to offer substituted 2-(piperazin-1yl)acetonitrile 7. The intermediate 7 can be oxidized by NiO$_2$—H$_2$O or MnO$_2$ in the presence of a wide range of NH$_2$-containing agents including NH$_3$, alkyl amine, aryl amine, heteroaryl amine, N,N-disubstituted hydrazine, O-substiuted hydroxyl amine, cyano amine, sulfonamide and sulfamide, to produce N-Boc piperazine amidines (*Tetrahedron Lett.* 2005, 46, 4919). The reaction solvent could be THF, DME, dioxane, DMF, EtOH, MeOH and water alone, or a mixture of two or three of these solvents and temperatures would range from ambient to reflux with ambient being the initial tmeperature evaluated. A well established deprotection of Boc group under acidic solution could provide piperazine amidine 2. TFA and HCl are the typical acids used for this deprotection, while the most commonly used solvents are ether and dichloromethane or the TFA itself, but other acidic agents and solvents could be used. Some selected references involving such reactions include 1) *Bioorg. Med. Chem. Lett.* 1996, 6, 2777; 2) *Zh. Org. Khim.* 1996, 32, 1010; 3) *J. Fluorine Chem.* 1996, 76, 177; 4) *Synth. Commun.* 1996, 26, 3549; 5) *J. Heterocycl. Chem.* 1994, 31, 841; 6) *J. Org. Chem.* 1964, 29, 794. The piperazine amidine 2 shown in FIG. 2a could be prepared via Scheme 2a.

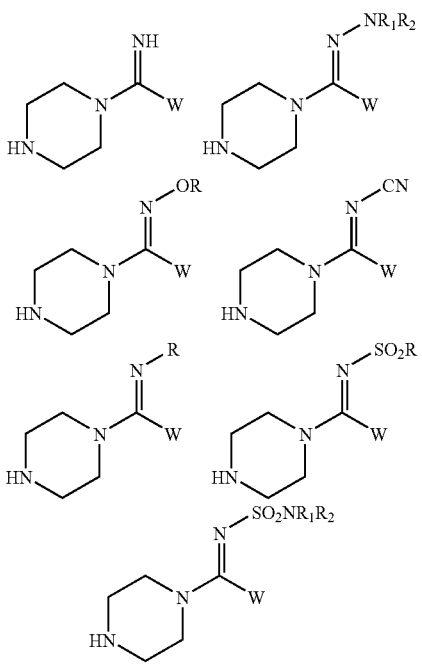

R includes alkyl, aryl group

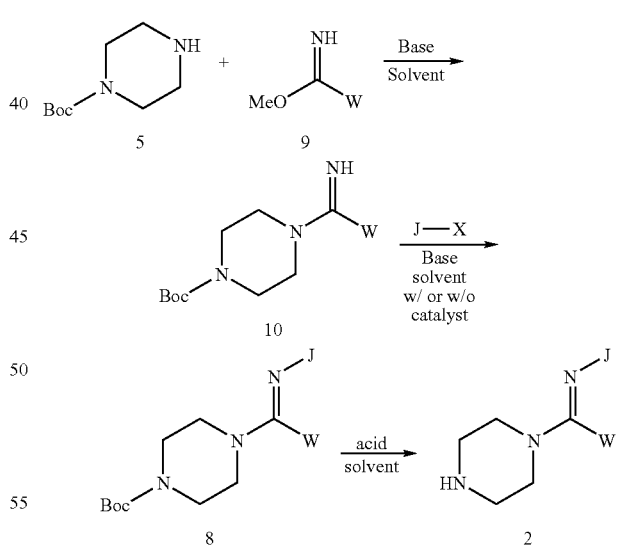

Scheme 2b depicts another general route that could be utilized to prepare piperazine amidine 2, and is exemplified by using N-Boc piperazine 5 as the starting material as well. In an aprotic (e.g., THF, DMF, DMSO, benzene) or protic solvent (e.g., MeOH, EtOH, PrOH, BuOH), at temperature ranging from room temperature to 150° C., either in the absence or presence of a base such as NaH, pyridine, Et$_3$N, di-Pr$_2$NEt, Na$_2$CO$_3$, K$_2$CO$_3$, N-Boc piperazine 5 could react with methyl arylimidate 9 to give N-Boc aryl piperazine amidine 10. The commercially available methyl arylimidate includes methyl benzimidate HCl from Aldrich Company and methyl picolinimidate from Research Organics Company. The primary amidine nitrogen of the intermediate 10 might be then transformed to a wide range of functionalities by reacting with different electrophiles in the presence or in the absence of catalyst at temperature from room temperature to 150° C. Preferred solvents would be aprotic solvents such as THF, dioxane, DME, DMF and DMSO. Bases could be selected from NaH, KH, pyridine, Et₃N, di-Pr₂NEt, Na₂CO₃, K₂CO₃, NaHMDS, LiHMDS, KHMDS, BuLi and LDA. Electrophiles that could be utilized in this sequence might include isocyanate, thioisocyanate, cyano halide, chloroformate, bromoformate, acyl halide, carbamyl halide, sulfonyl halide, sulfamoyl halide, alkyl halide or alkyl sulfonylate and aryl halide. Pd, Ni or Pt agents could be utilized as catalysts. The well precedented deprotection of amine by removal of the Boc group under acidic conditions would provide piperazine amidine 2. TFA and HCl are the typical acids utilized, while the most commonly used solvents are ether and dichloromethane or the TFA itself, but other acidic agents and solvents could be used. Some selected references involving such reactions were cited above in the section discussing Scheme 2a.

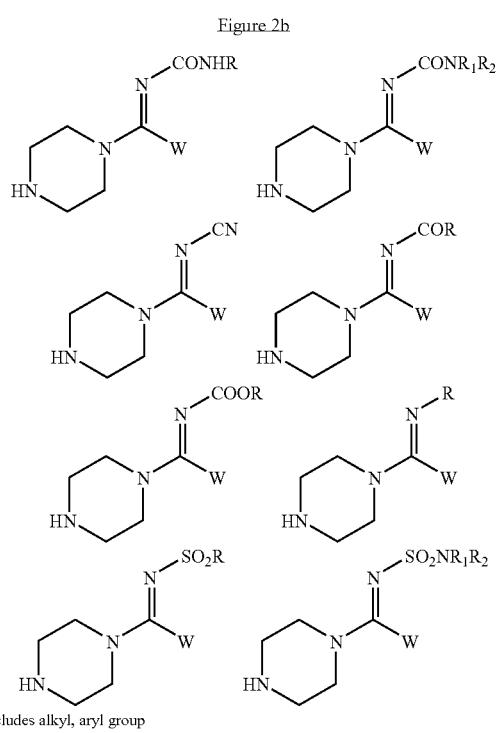

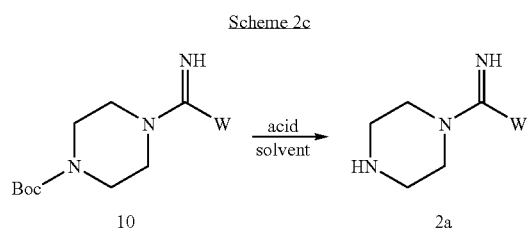

The Boc group in the intermediate 10 could be removed as previously described above for Scheme 2a, to provide piperazine amidine 2a. TFA and HCl are the typical solvents, while the most commonly used solvents are ether and dichloromethane, but other acidic agents and solvents could be used.

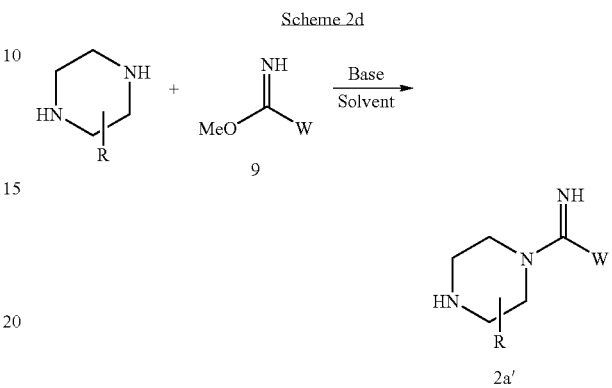

As shown in Scheme 2d, piperazines can also react with imidate 9 directly to provide piperazine amidines 2a'. Solvents can be an aprotic (e.g., THF, dioxane, DME, DMF, DMSO, benzene) or protic solvent (e.g., MeOH, EtOH, PrOH, BuOH). Base may not be needed for the reaction. When a base is required, it can be chosen from NaH, pyridine, Et₃N, di-Pr₂NEt, Na₂CO₃, K₂CO₃, NaOMe, NaOEt Na—O-tBu, and K—O-tBu. The reaction temperature can be selected from room temperature to 150° C.

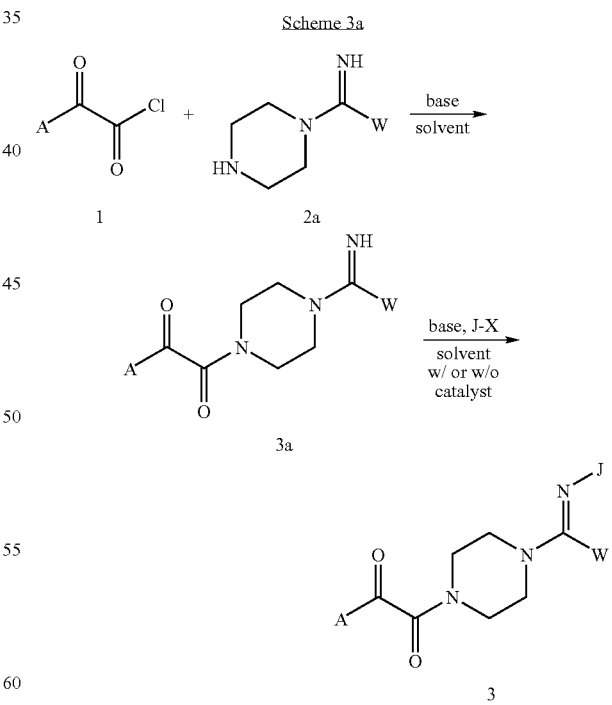

Scheme 3a depicts a general process to construct compound of Formula I from keto acyl chloride 1 and aryl piperazine methanimine 2a. An appropriate base (from catalytic to an excess amount) selected from sodium hydride, potassium carbonate, triethylamine, DBU, pyridine, DMAP or diisopropyl ethyl amine could be added into a solution of aryl piperazine methanimine 2a and keto acyl chloride 1 in an appropriate solvent selected from dichloromethane, chloroform, benzene, toluene, THF, diethyl ether, dioxane, acetone, N,N-dimethylformamide or pyridine at room temperature. The reaction could carried out at room temperature or up to 150° C. over a period of time (30 minutes to 16 hours) to afford the compounds of structure 3a. Some selected references involving such reactions include a) *Indian J. Chem., Sect B* 1990, 29, 1077; 2) *Chem. Sci.* 1998, 53, 1216; 3) *Chem. Pharm. Bull.* 1992, 40, 1481; 4) *Chem. Heterocycl. Compd.* 2002, 38, 539. The primary amidine nitrogen of the intermediate 3a could be functionalized to provide compounds of Formula I by reaction with an electrophile either in the presence or in the absence of catalyst at at temperature ranging from room temperature to 150° C. with room temperature being the initial temperature tried. The preferred solvents would be aprotic solvents such as THF, dioxane, DME, DMF and DMSO. Bases could be selected from either NaH, KH, pyridine, Et$_3$N, di-Pr$_2$NEt, Na$_2$CO$_3$, K$_2$CO$_3$, NaHMDS, LiHMDS, KHMDS, BuLi and LDA. The electrophile could be either an isocyanate, thioisocyanate, cyano halide, chloroformate, bromoformate, acyl halide, carbamyl halide, sulfonyl halide, sulfamoyl halide, alkyl halide or alkyl sulfonylate, or aryl halide. Pd, Ni or Pt agents could be utilized as catalysts if necessary. Some selected references involving functionization of imine nitrogen include 1) *Tetrahedron* 1969, 25, 5437; 2) *Khim-Farm. Zh.* 1996, 30, 29; 3) *Heterocycles* 1998, 48, 249; 4) *Tetrahedron Lett.* 1997, 38, 6367; 5) *J. Fluorine Chem.* 1996, 77, 175; 6) *Tetrahedron Lett.* 1995, 36, 6101; 7) *Heterocycles* 1993, 36, 2059; 8) *J. Org. Chem.* 1993, 58, 7406; 9) *Zh. Obshch. Khim.* 1992, 62, 1592; 10) *Arch. Pharm.* 1992, 325, 273; 11) *Zh. Org. Khim.* 1991, 27, 117; 12) *Synthesis* 1988, 122; 13) *Synthesis* 1988, 412; 14) *Chem. Ber.* 1986, 119, 2444; 15) *J Chem. Eng. Data.* 1968, 13, 142; 15) *Gazz. Chim. Ital.* 1961, 91, 216.

reagent. Many reagents for amide bond couplings are known by an organic chemist skilled in the art and nearly all of these are applicable for realizing the coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) *J. Chem. Soc. Chem Comm.* 1994, 201; (b) *J. Am. Chem. Soc.* 1994, 116,11580). Additionally, DEPBT (3-(diethoxyphosphoryloxy)-1,2,3-benzotriazin-4(3H)-one) and N,N-diisopropylethylamine, commonly known as Hunig's base, represents another efficient method to form the amide bond and provide compound 3a. DEPBT is either purchased from Adrich or prepared according to the procedure described in *Organic Lett.*, 1999, 1, 91. Typically an inert solvent such as DMF or THF is used but other aprotic solvents could be used. The primary amidine nitrogen of the intermediate 3a could be functionalized to provide compounds of Formula I by reaction with an electronphile either in the presence or in the absence of catalyst at temperature from room temperature to 150° C. Preferred solvents would be aprotic solvents such as THF, dioxane, DME, DMF and DMSO. The base could be selected from NaH, KH, pyridine, Et$_3$N, di-Pr$_2$NEt, Na$_2$CO$_3$, K$_2$CO$_3$, NaHMDS, LiHMDS, KHMDS, BuLi and LDA. The electrophile could be an isocyanate, thioisocyanate, cyano halide, chloroformate, bromoformate, acyl halide, carbamyl halide, sulfonyl halide, sulfamoyl halide, alkyl halide or alkyl sulfonylate, or aryl halide. Pd, Ni or Pt agents could be utilized as catalysts if necessary. Some selected references involving functionization of an imine nitrogen include 1) *Tetrahedron* 1969, 25, 5437; 2) *Khim-Farm. Zh.* 1996, 30, 29; 3) *Heterocycles* 1998, 48, 249; 4) *Tetrahedron Lett.* 1997, 38, 6367; 5) *J. Fluorine Chem.* 1996, 77, 175; 6) *Tetrahedron Lett.* 1995, 36, 6101; 7) *Heterocycles* 1993, 36, 2059; 8) *J. Org. Chem.* 1993, 58, 7406; 9) *Zh. Obshch. Khim.* 1992, 62, 1592; 10) *Arch. Pharm.* 1992, 325, 273; 11) *Zh. Org. Khim.* 1991, 27, 117; 12) *Synthesis* 1988, 122; 13) *Synthesis* 1988, 412; 14) *Chem. Ber.* 1986, 119, 2444; 15) *J Chem. Eng. Data.* 1968, 13, 142; 15) *Gazz. Chim. Ital.* 1961, 91, 216.

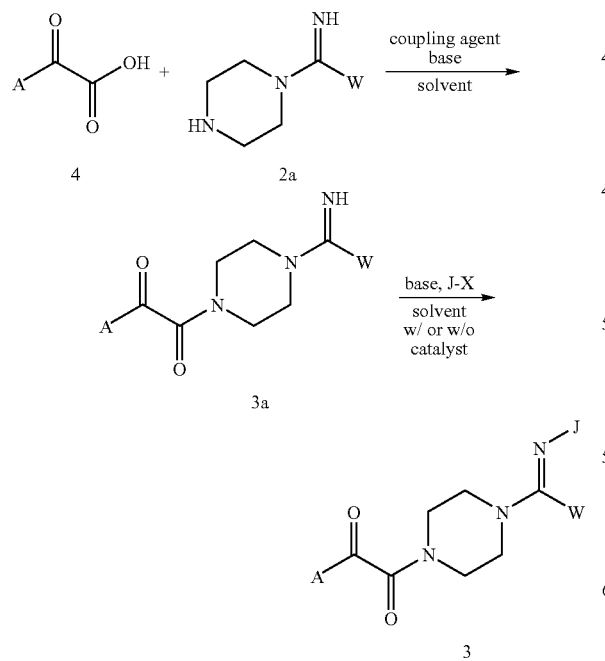

Scheme 3b

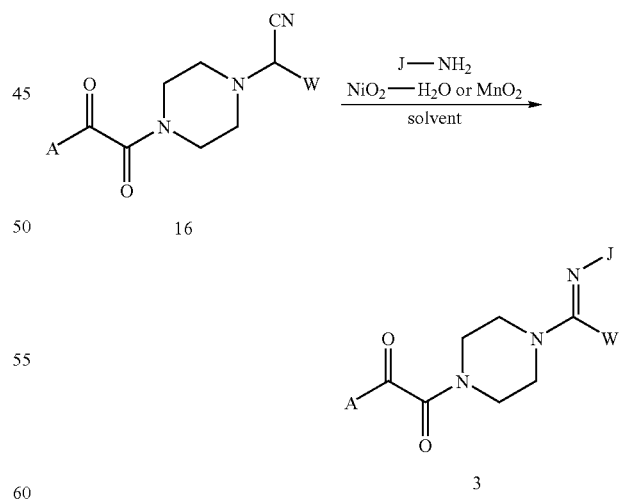

Scheme 4

Alternatively, as shown in Scheme 3b, the aryl piperazine methanimine 2a could be coupled with a keto acid 4 using a standard amide bond or peptide bond forming coupling Compounds of Formula I could also be synthesized from an aryl piperazine acetonitrile intermediate 16 by oxidization using NiO$_2$—H$_2$O or MnO$_2$ in the presence of an NH$_2$-containing agent including NH$_3$, alkyl amine, aryl amine, heteroaryl amine, N,N-disubstituted hydrazine, O-substiuted hydroxyl amine, cyano amine, sulfonamide, or sulfamide (Scheme 4, *Tetrahedron Lett.* 2005, 46, 4919). An excess amount of NiO$_2$—H$_2$O or MnO$_2$ could be added into a solution of compound 16 and the NH2-containing agent in solvent to afford compound 3. THF, DME, dioxane, DMF, EtOH, MeOH and water alone, or their mixture, can be utilized as the solvent.

Scheme 5

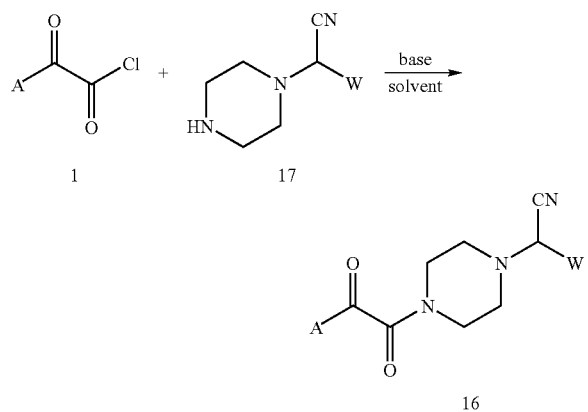

Aryl piperzine acetonitrile intermediate 16 could be prepared via a reaction of a 2-keto acyl halide, such as compound 1, and piperazine acetonitrile 17, as shown in Scheme 5. An appropriate base (from catalytic to an excess amount) selected from sodium hydride, potassium carbonate, triethylamine, DBU, pyridine, DMAP or di-isopropyl ethyl amine would be added into a solution of the aryl piperazine acetonitrile 2a and the 2-keto acyl chloride 1 in an appropriate solvent selected from dichloromethane, chloroform, benzene, toluene, THF, diethyl ether, dioxane, acetone, N,N-dimethylformamide or pyridine at room temperature. Then the reaction was carried out at either room temperature or an appropriate temperature up to 150° C. over a period of time (30 minutes to 16 hours) to afford the structure of 16. Some selected references involving such reactions include a) *Indian J. Chem., Sect B* 1990, 29, 1077; 2) *Chem. Sci.* 1998, 53, 1216; 3) *Chem. Pharm. Bull.* 1992, 40, 1481; 4) *Chem. Heterocycl. Compd.* 2002, 38, 539.

Scheme 6

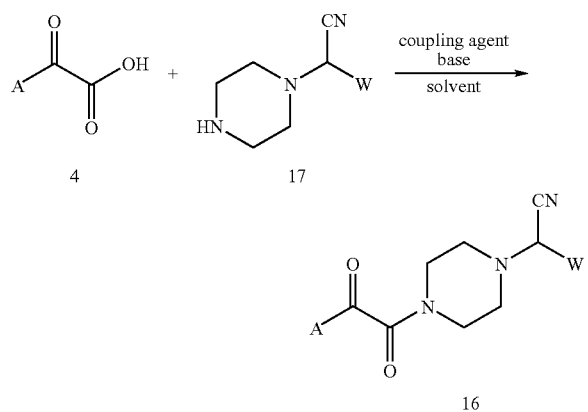

As shown in Scheme 6, an aryl piperazine acetonitrile 17 could be coupled with a 2-keto acid 4 using standard amide bond or peptide bond forming coupling reagents. Many reagents for amide bond couplings are known by an organic chemist skilled in the art and nearly all of these are applicable for realizing coupled amide products. The combination of EDAC and triethylamine in tetrahydrofuran or BOPCl and diisopropyl ethyl amine in chloroform have been utilized most frequently but DEPBT, or other coupling reagents such as PyBop could be utilized. Another useful coupling condition employs HATU ((a) *J. Chem. Soc. Chem Comm.* 1994, 201; (b) *J. Am. Chem. Soc.* 1994, 116,11580). Additionally, DEPBT (3-(diethoxyphosphoryloxy)-1,2,3-benzotriazin-4 (3H)-one) and N,N-diisopropylethylamine, commonly known as Hunig's base, represents another efficient method to form the amide bond and provide compound 16. DEPBT is either purchased from Adrich or prepared according to the procedure described in *Organic Lett.*, 1999, 1, 91. Typically an inert solvent such as DMF or THF is used but other aprotic solvents could be used.

Scheme 7

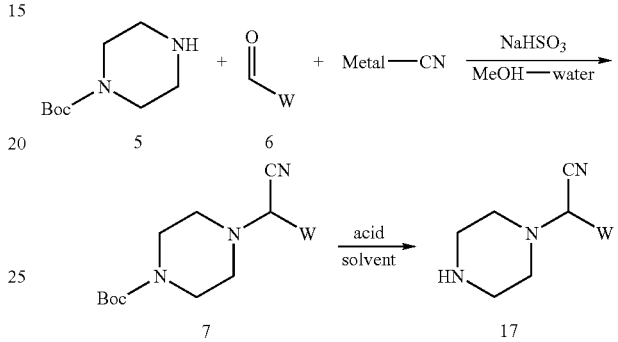

Aryl piperazine acetonitrile 17 could be prepared via a Strecker reaction involving N-Boc piperazine, an aryl aldehyde and a cyanide agent, followed by removal of Boc group from N atom under acidic condition as described afore. In the Strecker reaction, the cyanide agent can be selected from TMS—CN, NaCN, KCN, Al(CN)$_3$, Zn(CN)$_2$, CuCN, or HCN (gas or solution). The solvent could be an aprotic (e.g., THF, DMF, DMSO, benzene) or protic solvent (e.g., MeOH, EtOH, PrOH, BuOH, water). Usually a protic solvent or a co-solvent with a protic component is preferred. Some selected references involving Strecker reactions include a) *Aust. J. Chem.* 1997, 50, 747; b) *Tetrahedron* 1997, 53, 8941; c) *Can. J. Chem.* 1996, 74, 88; d) *J. Org. Chem.* 1995, 60, 588; e) *Synthesis* 1995, 659; f) *Chem. Ber.* 1994, 127, 1761.

Reaction conditions and methods given in the specific examples are broadly applicable to compounds with other substitution and to other tranformations in this application.

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ (δ$_H$ 7.26), CD$_3$OD (δ$_H$ 3.30), and DMSO-d6 (δ$_H$ 2.50). Standard acronyms were employed to describe the multiplicity patterns: s (singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV—Vis detector with Mass Spectrometry (MS) data determined using a Micromass Platform for LC in electrospray mode.

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods (i.e., Compound Identification)
Column A: Xterra MS C18 5 um 4.6×30 mm column
Column B: Phenomenex 5 u C18 4.6×30 mm column
Column C: Xterra MS C18 4.6×30 mm column
Column D: Phenomenex 4.6×50 mm C18 5 um column
Column E: Xterra 4.6×30 mm S5 column
Column F: Phenomenex-Luna 4.6×50 mm S10 column
Column G: Phenomenex 10 u 3.0×50 mm column
Column H: Luna 4.6×50 mm column
Column I: Phenomenex 4.6×30 mm 10 u column
Gradient: 100% Solvent A/0% Solvent B to 0% Solvent A/100% Solvent B
Gradient time: 2 minutes
Hold time 1 minute
Flow rate: 5 ml/min
Detector Wavelength: 220 nm Solvent System I
Solvent A: 10% MeOH/90% H$_2$O/0.1% Trifluoroacetic Acid
Solvent B: 10% H$_2$O/90% MeOH/0.1% Trifluoroacetic Acid Solvent System II
Solvent A: 5% MeCN/95% H$_2$O/10 mm ammonium acetate
Solvent B: 95% MeCN/5% H$_2$O/10 mm ammonium acetate All the LC-MS in the following sections, except which are specified using solvent system II, were obtained by using solvent system I.

Compounds purified by preparative HPLC were diluted in methanol (1.2 ml) and purified using the following methods on a Shimadzu LC-10A automated preparative HPLC system.

Preparative HPLC Method (i.e., Compound Purification)
Purification Method: Initial gradient (40% B, 60% A) ramp to final gradient (100% B, 0% A) over 20 minutes, hold for 3 minutes (100% B, 0% A)
Solvent A: 10% MeOH/90% H$_2$O/0.1% Trifluoroacetic Acid
Solvent B: 10% H$_2$O/90% MeOH/0.1% Trifluoroacetic Acid
Column: YMC C18 S5 20×100 mm column
Detector Wavelength: 220 nm Typical Procedures and Characterization of Selected Examples:
Typical Procedure to Prepare Amide Derivatives from Amino-Indole Procusors General Procedures:

Preparation of N-Boc Piperazine Amidine Intermedates:

Method I

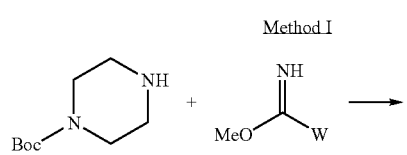

-continued

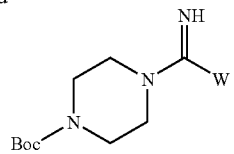

To a solution of tert-butyl-1-piperazinecarboxylate (1-1.5 eq.) and aryl imidate (1 eq.) in EtOH, was added an excess amount of Et$_3$N (5-20 eq.). The reaction mixture was stirred at rt for 17 h and then was concentrated in vacuo to provide a residue. The residue was partitioned between NaHCO$_3$ and EtOAc and the organic layer was extracted with EtOAc. Then, the combined organic layer was dried over MgSO$_4$, filtered and the filtrate was concentrated to the N-Boc piperazine amidine, which was used in the further reactions without any purification.

A Specific Example

Preparation of tert-butyl 4-(imino(phenyl)methyl)piperazine-1-carboxylate

To a solution of tert-butyl-1-piperazinecarboxylate (25 g) and methyl phenyl imidate HCl salt (20 g) in EtOH (500 ml), was added an excess amount of Et$_3$N (50 ml). The reaction mixture was stirred at room temperature for 17 hours and then was concentrated in vacuo to provide a residue. The residue was partitioned between NaHCO$_3$ (200 ml) and EtOAc (200 ml), and the organic layer was extracted with EtOAc (3×200 ml). Then, the combined organic layer was dried over MgSO$_4$, filtered and the filtrate was concentrated to tert-butyl 4-(imino(phenyl)methyl)piperazine-1-carboxylate, which was used in the further reactions without any purification.

Method II

An excess of base (1-20 eq.), such as Et$_3$N, iPr$_2$NEt or NaH, was added to a solution of N-Boc piperazine amidine (1 eq.) in THF, followed by addition of electrophile (1 to 10 eq.). The reaction was stirred for 17 hours then was quenched with saturated aqueous NaHCO$_3$. The aqueous phase was extracted with EtOAc. The combined organic layer was dried over MgSO₄, filtered, and the filtrate concentrated to a residue, which was used in the further reactions without purification, or purified by silica gel column chromatography or Shimadzu automated preparative HPLC System.

A Specific Example

Preparation of tert-butyl 4-(cyanamido(phenyl)methyl)piperazine-1-carboxylate

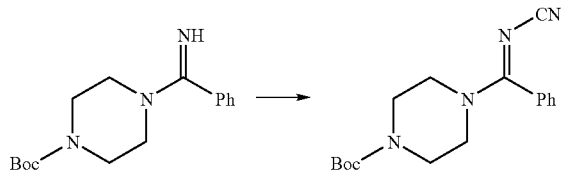

Et₃N (10 ml) was added to a solution of tert-butyl 4-(imino(phenyl)methyl)piperazine-1-carboxylate (2 g) in THF (50 ml), followed by addition of Br—CN (4 g). The reaction was stirred for 17 hours then was quenched with saturated aqueous NaHCO₃ (50 ml) The aqueous phase was extracted with EtOAc (3×50 ml). The combined organic layer was dried over MgSO₄, filtered, and the filtrate concentrated to a crude tert-butyl 4-(cyanamido(phenyl)methyl)piperazine-1-carboxylate, which was used in the further reactions without purification.

Method III

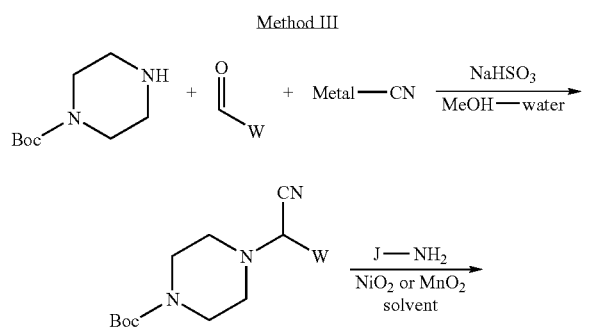

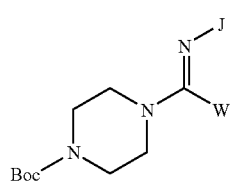

Step 1: A solution of aldehyde (1 eq.) in MeOH was added into a aqueous solution of NaHSO₃ (1-5 eq.), followed by amine (1-2 eq.) in aqueous MeOH. The mixture was cooled before the addition of cyanide (2-10 eq.) in water. After stirred for 24 hours at room temperature, ethyl ether was added. The organic layer was separated, washed with water, dried under MgSO₄ and concentrated to give a residue, which was purified by silica gel column chromatography to afford aryl piperazine acetonitrile.

Step 2: An excess amount of NiO₂—H₂O or MnO₂ (5-100 eq.) was added into a solution of aryl piperazine acetonitrile (1 eq.) and amine (5-100 eq.) in THF or DMF. The reaction mixture was stirred for 1-5 days. The solids were then removed by filtration. The filtrate was concentrated under vaccum to give a residure which was purified by silica gel column chromatography or Shimadzu automated preparative HPLC System.

A Specific Example

Preparation of tert-butyl 4-(cyanamido(phenyl)methyl)piperazine-1-carboxylate

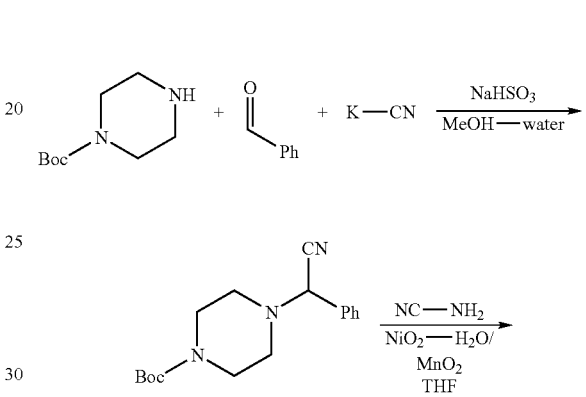

Step 1: A solution of aldehyde (570 mg) in MeOH (10 ml) was added into a aqueous solution of NaHSO₃ (645 mg) in water (10 ml), followed by amine (1 g) in aqueous MeOH (10 ml). The mixture was cooled before the addition of cyanide (700 mg) in water. After stirring for 24 hours at room temperature, ethyl ether (50 ml) was added. The organic layer was separated, washed with water (20 ml), dried under MgSO₄ and concentrated to give a residue, which was purified by silica gel column chromatography to afford tert-butyl 4-(cyano(phenyl)methyl)piperazine-1-carboxylate.

Step 2: An excess amount of NiO₂—H₂O (25 g) was added into a solution of tert-butyl 4-(cyano(phenyl)methyl)piperazine-1-carboxylate (10 g) and cyanamine (7 g) in THF (100 ml). An additional cyanamine (25 g) and MnO2 (100 g) was added after 24 hours, and then the reaction was kept stirring for 5 days. The solids were removed by filtration. The filtrate was concentrated under vaccum to give a residue which was purified by silica gel column chromatography to provide tert-butyl 4-(cyanamido(phenyl)methyl)piperazine-1-carboxylate.

Characterization of N-Boc Piperazine Amidine Intermedates (Table A):

TABLE A

| Compd. Number | Structure | Method Used | MS (M + H)+ Calcd. | MS (M + H)+ Observ. And Retention Time and NMR |
|---|---|---|---|---|
| Boc-01 | 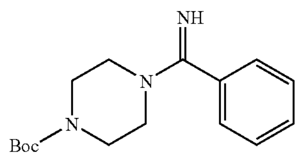 | I | 290.19 | 290.23<br>Rf = 1.93 min<br>(column E) |
| Boc-02 | 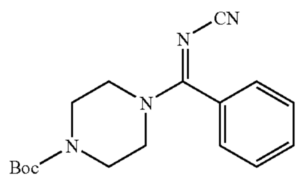 | II, III | 315.18 | 315.25<br>Rf = 2.17 min<br>(column E) |
| Boc-03 | 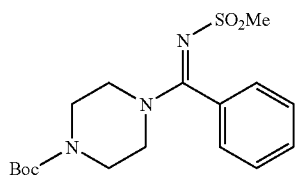 | II | 368.16 | 368.19<br>Rf = 2.19 min<br>(column E) |
| Boc-04 | 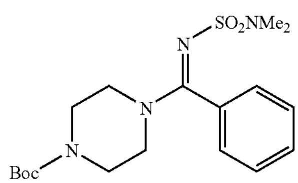 | II | 397.16 | 397.22<br>Rf = 2.32 min<br>(column E) |
| Boc-05 | 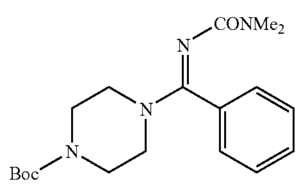 | II | 361.22 | 361.24<br>Rf = 2.24 min<br>(column E) |
| Boc-06 | 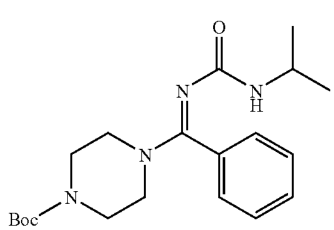 | II | 375.24 | 375.36<br>Rf = 2.01 min<br>(column E) |
| Boc-07 | 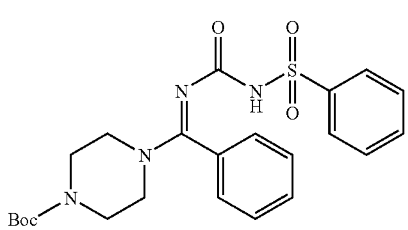 | II | 473.19 | 473.23<br>Rf = 2.26 min<br>(column E) |

TABLE A-continued

| Compd. Number | Structure | Method Used | MS (M + H)+ Calcd. | MS (M + H)+ Observ. And Retention Time and NMR |
|---|---|---|---|---|
| Boc-08 | 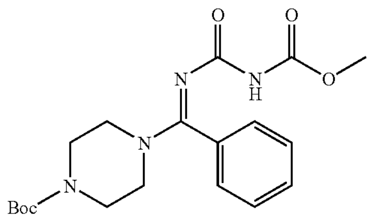 | II | 391.20 | 391.25<br>Rf = 2.10 min<br>(column E) |
| Boc-09 | 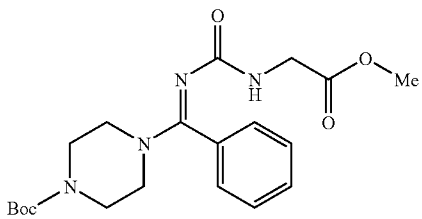 | II | 405.21 | 405.27<br>Rf = 1.93 min<br>(column E) |
| Boc-10 | 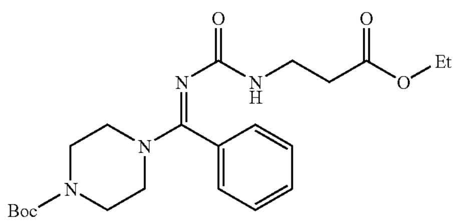 | II | 433.25 | 433.38<br>Rf = 2.15 min<br>(column E) |
| Boc-11 | 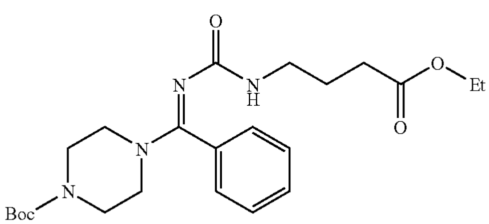 | II | 447.26 | 447.32<br>Rf = 2.12 min<br>(column E) |
| Boc-12 | 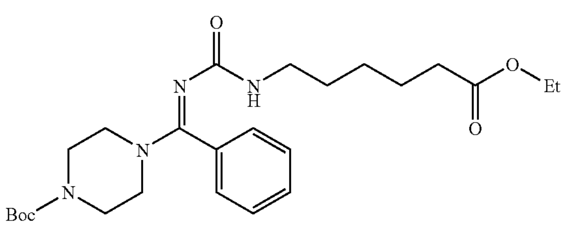 | II | 475.28 | 475.36<br>Rf = 2.21 min<br>(column E) |
| Boc-13 | 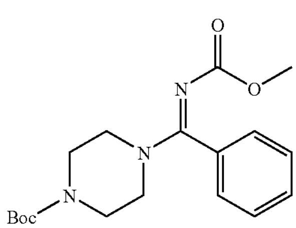 | II | 348.19 | 348.22<br>Rf = 2.06 min<br>(column E) |
| Boc-14 | 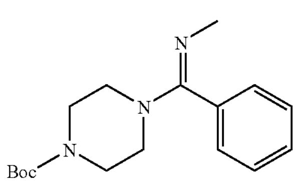 | II | 304.2 | 304.27<br>Rf = 1.59 min<br>(column E) |

TABLE A-continued

| Compd. Number | Structure | Method Used | MS (M + H)+ Calcd. | MS (M + H)+ Observ. And Retention Time and NMR |
|---|---|---|---|---|
| Boc-15 | 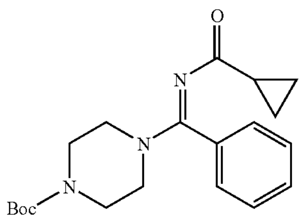 | II | 358.21 | 358.24<br>Rf = 1.77 min<br>(column E) |
| Boc-16 | 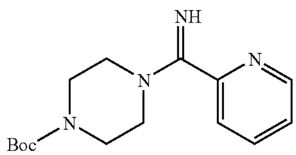 | I | 291.18 | 291.28<br>Rf = 1.62 min<br>(column E) |
| Boc-17 | 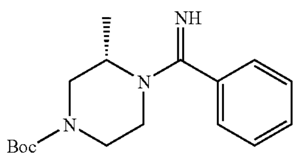 | I | 304.2 | 304.26<br>Rf = 1.84 min<br>(column E) |
| Boc-18 | 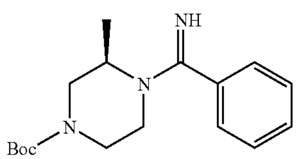 | I | 304.2 | 304.31<br>Rf = 1.86 min<br>(column E) |
| Boc-19 | 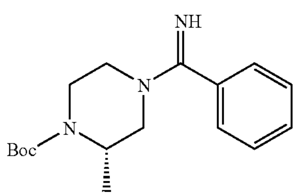 | I | 304.2 | 304.26<br>Rf = 1.84 min<br>(column E) |
| Boc-20 | 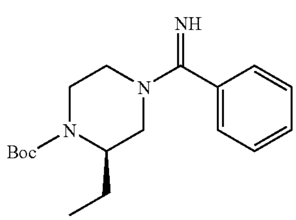 | I | 318.22 | 318.30<br>Rf = 1.97 min<br>(column E) |
| Boc-21 | 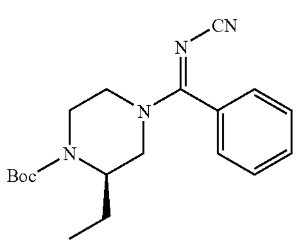 | II | 343.21 | 343.28<br>Rf = 2.30 min<br>(column E) |

TABLE A-continued

| Compd. Number | Structure | Method Used | MS (M + H)+ Calcd. | MS (M + H)+ Observ. And Retention Time and NMR |
|---|---|---|---|---|
| Boc-22 | 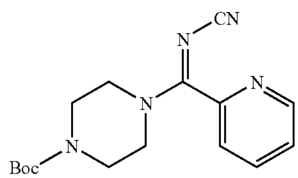 | II | 316.18 | 316.25<br>Rf = 1.94 min<br>(column E) |
| Boc-23 | 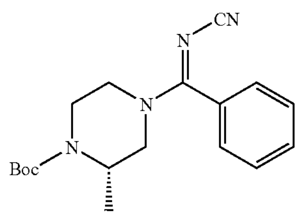 | II | 329.2 | 329.27<br>Rf = 2.23 min<br>(column E) |
| Boc-24 | 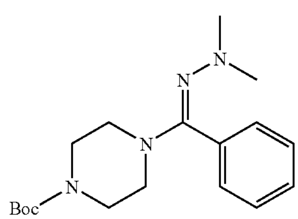 | III | 333.23 | 333.30<br>Rf = 1.86 min<br>(column E) |

Preparation of Piperazine Amidine Intermedates:

Method 1

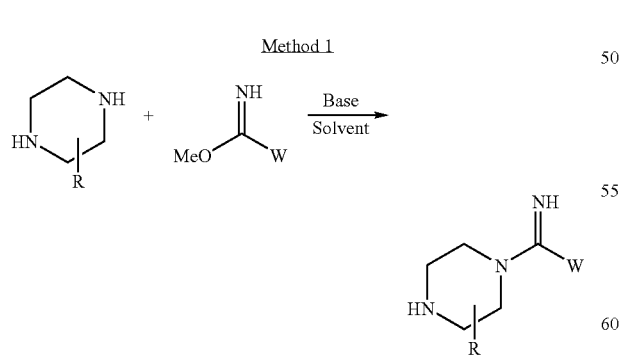

Piperazine derivative (1 eq.) and aryl imidate (1 eq.) in EtOH was stirred at room temperature for 17 hours and then was concentrated in vacuo to provide a residue, which was used in the further reactions without any purification.

An Specific Example

Preparation of
®-(3-methylpiperazin-1-yl)(phenyl)methanimine

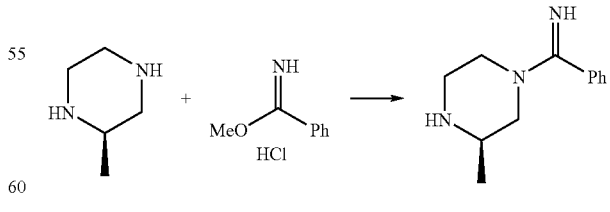

®-Methyl piperazine (2 g) and methyl phenyl imidate HCl salt (3.44 g) in EtOH (20 ml) was stirred at room temperature for 17 hours and then was concentrated in vacuo to provide crude ®-(3-methylpiperazin-1-yl)(phenyl)methanimine, which was used in the further reactions without any purification.

Method 2

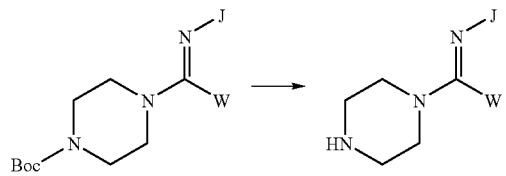

N-Boc piperazine amidine derivative was dissolved in an acidic solution of TFA or HCl in CH$_2$Cl$_2$, ether, dioxane or alcohol. After 0.5 to 17 hours, the solution was concentrated under vaccum to give an salt residue, which was used in the next step without purification. Or, salt precipitated out from solution, which was washed with CH$_2$Cl$_2$, ether, dioxane or alcohol before further use.

An Specific Example

Preparation of (phenyl(piperazin-1-yl)methylene)cyanamide hydrochloride

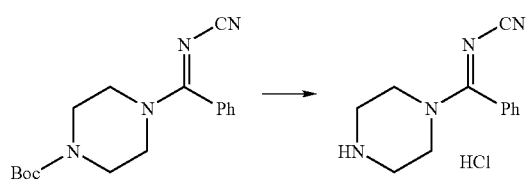

tert-Butyl 4-(cyanamido(phenyl)methyl)piperazine-1-carboxylate (1.5 g) was dissolved in 16 ml of 2M HCl in dioxane. After four hours, the solution was diluted with dioxane (20 ml) and the solid, (phenyl(piperazin-1-yl)methylene)cyanamide hydrochloride (1 g), was collected via filtration. It was washed with ether before further use.

Characterization of Piperazine Amidine Intermedates (Table B):

TABLE B

| Compd. Number | Structure | Method Used | MS (M + H)$^+$ Calcd. | MS (M + H)$^+$ Observ. And Retention Time and NMR |
|---|---|---|---|---|
| FP-01 | 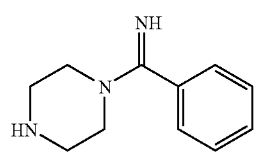 | 2 | 190.13 | 190.21 Rf = 0.25 min (column E) |
| FP-02 | 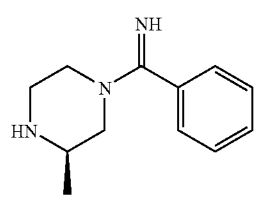 | 1 | 204.15 | 204.21 Rf = 0.28 min (column E) |
| FP-03 | 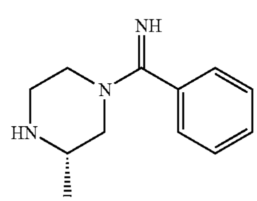 | 1, 2 | 204.15 | 204.21 Rf = 0.32 min (column E) |
| FP-04 | 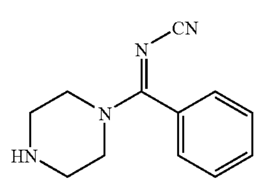 | 2 | 215.13 | 215.20 Rf = 0.41 min (column E) |

TABLE B-continued

| Compd. Number | Structure | Method Used | MS (M + H)+ Calcd. | MS (M + H)+ Observ. And Retention Time and NMR |
|---|---|---|---|---|
| FP-05 | (piperazine-C(=N-SO₂Me)-phenyl) | 2 | 268.11 | 268.19<br>Rf = 0.36 min<br>(column E) |
| FP-06 | (piperazine-C(=N-SO₂NMe₂)-phenyl) | 2 | 297.14 | 297.27<br>Rf = 0.59 min<br>(column E) |
| FP-07 | (piperazine-C(=N-CONMe₂)-phenyl) | 2 | 261.17 | 261.30<br>Rf = 0.81 min<br>(column E) |
| FP-08 | (piperazine-C(=N-C(=O)NH-CH₂-C(=O)OEt)-phenyl) | 2 | 319.18 | 319.25<br>Rf = 1.14 min<br>(column E) |
| FP-09 | (piperazine-C(=N-C(=O)NH-(CH₂)₂-C(=O)OEt)-phenyl) | 2 | 333.19 | 333.24<br>Rf = 1.49 min<br>(column E) |
| FP-10 | (piperazine-C(=N-C(=O)NH-(CH₂)₃-C(=O)OEt)-phenyl) | 2 | 347.01 | 347.26<br>Rf = 1.49 min<br>(column E) |
| FP-11 | (piperazine-C(=N-C(=O)NH-(CH₂)₄-C(=O)OEt)-phenyl) | 2 | 375.24 | 375.29<br>Rf = 1.77 min<br>(column E) |

TABLE B-continued

| Compd. Number | Structure | Method Used | MS (M + H)+ Calcd. | MS (M + H)+ Observ. And Retention Time and NMR |
|---|---|---|---|---|
| FP-12 | 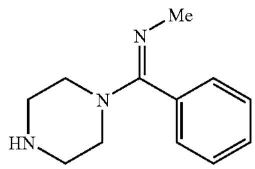 | 2 | 204.15 | 204.22<br>Rf = 0.28 min<br>(column E) |
| FP-13 | 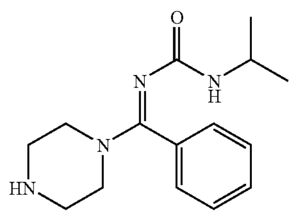 | 2 | 275.19 | 275.25<br>Rf = 1.25 min<br>(column E) |
| FP-14 | 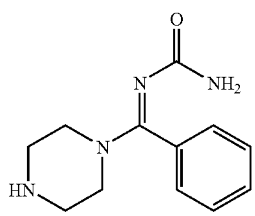 | 2 | 233.14 | 233.22<br>Rf = 0.32 min<br>(column E) |
| FP-15 | 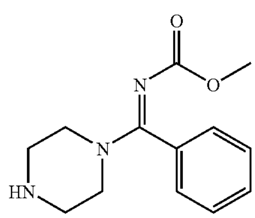 | 2 | 248.14 | 248.21<br>Rf = 0.67 min<br>(column E) |
| FP-16 | 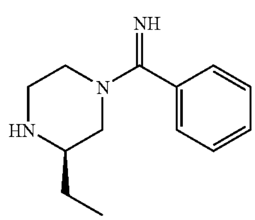 | 2 | 218.17 | 218.24<br>Rf = 0.39 min<br>(column E) |
| FP-17 | 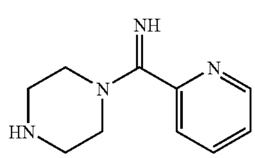 | 2 | 191.13 | 191.22<br>Rf = 0.21 min<br>(column E) |
| FP-18 | 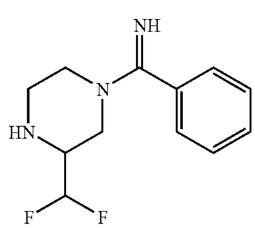 | 1 | 240.13 | 240.24<br>Rf = 0.32 min<br>(column E) |

TABLE B-continued

| Compd. Number | Structure | Method Used | MS (M + H)+ Calcd. | MS (M + H)+ Observ. And Retention Time and NMR |
|---|---|---|---|---|
| FP-19 | 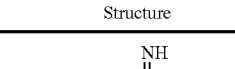 | 1 | 222.14 | 222.24 Rf = 0.30 min (column E) |

Preparation of the Compounds of Formula I:

Method A

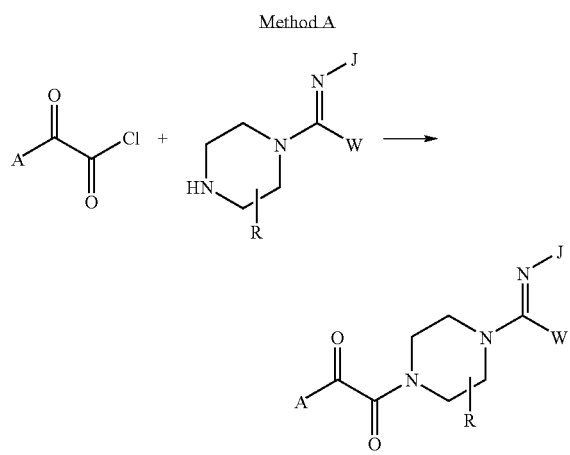

Et₃N (1-100 eq.) was added into a solution of 2-keto acyl chloride (1 eq.) and piperazine (1-5 eq.) in an aprotic solvent (such as THF, DMF, dioxane, ether, acetonitrile) and reaction was stirred at room temperature for 17 hours before quenched with saturated aqueous NaHCO₃ solution. The aqueous layer was extracted with ethyl acetate. The organic phase combined and dried over anhydrous MgSO₄. Concentration in vacuo provided a crude product, which was purified by tritaration, or recrystallization, or silica gel column chromatography, or Shimadzu automated preparative HPLC System.

An Specific Example

Preparation of 1-(4-fluoro-1H-indol-3-yl)-2-(4-(imino(phenyl)methyl)piperazin-1-yl)ethane-1,2-dione

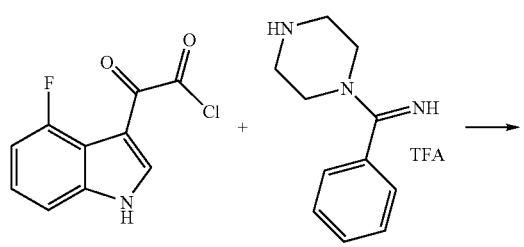

-continued

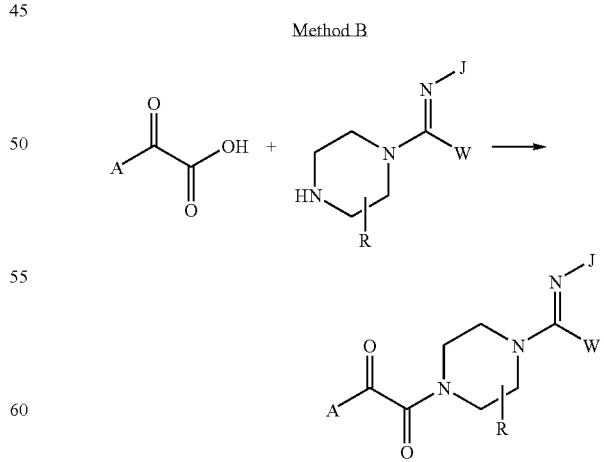

Et₃N (2 ml) was added into a solution of 2-(4-fluoro-1H-indol-3-yl)-2-oxoacetyl chloride (1.56 g) and phenyl(piperazin-1-yl)methanimine TFA salt (1.98 g) in THF (20 ml) and reaction was stirred at room temperature for 17 hours before quenched with saturated aqueous NaHCO₃ solution (50 ml). The aqueous layer was extracted with ethyl acetate (3×50 ml). The organic phase combined and dried over anhydrous MgSO₄. Concentration in vacuo provided a crude product, which was purified by silica gel column chromatography to afford 1-(4-fluoro-1H-indol-3-yl)-2-(4-(imino(phenyl)methyl)piperazin-1-yl)ethane-1,2-dione.

Method B

2-Keto acid (1 eq.), piperazine (1-5 eq.), 3-(diethoxyphosphoryloxy)-1,2,3-benzotriazin-4(3H)-one (DEPBT) (1-5 eq.) and Hunig's Base (1-100 eq.) were combined in DMF. The mixture was stirred at room temperature for 17 hours.

DMF was removed via evaporation at reduced pressure and the residue was partitioned between ethyl acetate and 5-10% Na$_2$CO$_3$ aqueous solution. The aqueous layer was extracted with ethyl acetate. The organic phase combined and dried over anhydrous MgSO$_4$. Concentration in vacuo provided a crude product, which was purified by tritaration, or recrystallization, or silica gel column chromatography, or Shimadzu automated preparative HPLC System.

An Specific Example

Preparation of ((4-(2-(4-fluoro-7-(1H-1,2,3-triazol-1-yl)-1H-pyrrolo[2,3-c]pyridin-3-yl)-2-oxoacetyl)piperazin-1-yl)(phenyl)methylene)cyanamide

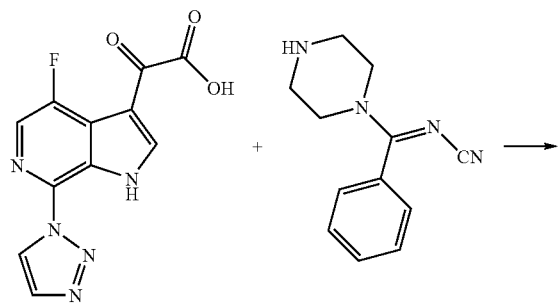

2-(4-fluoro-7-(1H-1,2,3-triazol-1-yl)-1H-pyrrolo[2,3-c]pyridin-3-yl)-2-oxoacetic acid (100 mg), (phenyl(piperazin-1-yl)methylene)cyanamide (77 mg), DEPBT (108 mg) and iPr$_2$NEt (0.2 ml) were combined in DMF (2 ml). The reaction mixture was stirred at room temperature for 17 hours before diluted with 10% Na$_2$CO$_3$ in water (5 ml). The aqueous solution was extracted with EtOAc (3×20 ml). The organic layer was combined, dried over MgSO$_4$ and concentrated. The residue was tritarated with MeOH (5 ml) and the resultant solid was collected by filtration to give ((4-(2-(4-fluoro-7-(1H-1,2,3-triazol-1-yl)-1H-pyrrolo[2,3-c]pyridin-3-yl)-2-oxoacetyl)piperazin-1-yl)(phenyl)methylene)cyanamide (5 mg).

Method C

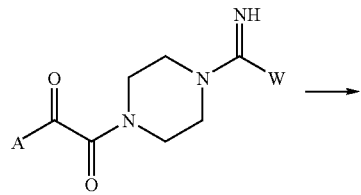

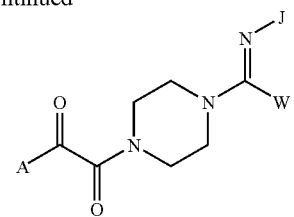

An excess of base (1-20 eq., such as Et$_3$N, iPr$_2$NEt or NaH), was added to a solution of 2-keto acyl piperazine amidine (1 eq.) in THF, followed by addition of electrophile (1 to 10 eq.). The reaction was stirred for 17 hours then was quenched with saturated aqueous NaHCO$_3$. The aqueous phase was extracted with EtOAc. The combined organic layer was dried over MgSO$_4$, filtered, and the filtrate concentrated to a residue, which was used in the further reactions without purification, or purified by silica gel column chromatography or Shimadzu automated preparative HPLC System.

An Specific Example

Preparation of (((R)-4-(2-(4-fluoro-7-(1H-1,2,3-triazol-1-yl)-1H-pyrrolo[2,3-c]pyridin-3-yl)-2-oxoacetyl)-3-methylpiperazin-1-yl)(phenyl)methylene)cyanamide

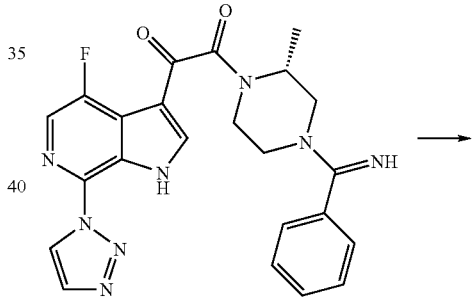

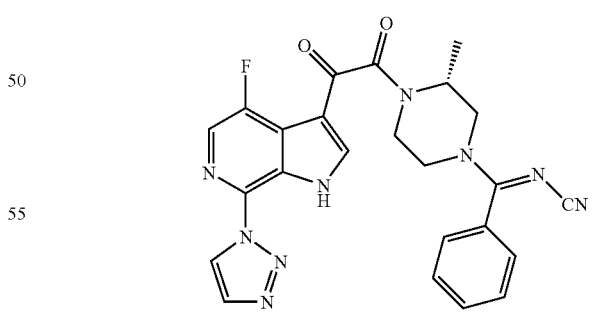

Et$_3$N (0.5 ml) was added to a solution of 1-(4-fluoro-7-(1H-1,2,3-triazol-1-yl)-1H-pyrrolo[2,3-c]pyridin-3-yl)-2-((R)-4-(imino(phenyl)methyl)-2-methylpiperazin-1-yl)ethane-1,2-dione (100 mg) in THF (10 ml), followed by addition of Br—CN (210 mg). The reaction was stirred for 17 hours then was quenched with saturated aqueous NaHCO$_3$ (10 ml) The aqueous phase was extracted with EtOAc (3×10 ml). The combined organic layer was dried over MgSO$_4$, filtered, and the filtrate concentrated to a crude tert-butyl 4-(cyanamido(phenyl)methyl)piperazine-1-carboxylate, which was purified by using Shimadzu automated preparative HPLC System.

Method D

An excess amount of NiO$_2$—H$_2$O or MnO$_2$ (5-100 eq.) was added into a solution of 2-keto acyl piperazine acetonitrile (1 eq.) and amine (5-100 eq.) in THF or DMF. The reaction mixture was stirred for 1-5 days. The solids were then removed by filtration. The filtrate was concentrated under vaccum to give a residure which was purified by silica gel column chromatography or Shimadzu automated preparative HPLC System.

An Specific Example

Preparation of 1-(4-fluoro-1H-indol-3-yl)-2-(4-(phenyl(phenylimino)methyl)piperazin-1-yl)ethane-1,2-dione An excess amount of MnO$_2$ (500 mg) was added into a solution of 2-(4-(2-(4-fluoro-1H-indol-3-yl)-2-oxoacetyl) piperazin-1-yl)-2-phenylacetonitrile (100 mg) and aniline (0.5 ml) in DMF (10 ml), and the reaction was kept stirring for 2 days. The solids were removed by filtration. The filtrate was concentrated under vaccum to give a residure which was purified by using Shimadzu automated preparative HPLC System to afford 1-(4-fluoro-1H-indol-3-yl)-2-(4-(phenyl (phenylimino)methyl)piperazin-1-yl)ethane-1,2-dione.

Method E

X = C, N
Y = F, OMe
Z = Cl, Br

An excess amount of stanny or boron agents (2-10 eq.) was added into a solution of indole or azaindole halide (1 eq.) and palladium (1-30%) in dioxane or DMF. The reaction mixture was heated to 50 to 170° C. for 1-5 days. The solids were then removed by filtration. The filtrate was concentrated under vaccum to give a residure which was purified by silica gel column chromatography or Shimadzu automated preparative HPLC System.

Characterization of the Compounds of Formula I (Table C):

TABLE C

| Compd. Number | Product's Structure | Method Used | MS (M + H)+ Calcd. | MS (M + H)+ Observ. And Retention Time and NMR |
|---|---|---|---|---|
| AM-01 | | A | 379.16 | 379.20<br>Rf = 1.38 min<br>(column D) |
| AM-02 | | A | 404.15 | 404.07<br>Rf = 1.10 min<br>(column B, solvent system II) |
| AM-03 | | B | 447.18 | See additional experimental procedure section |
| AM-04 | | D | 468.17 | 468.13<br>Rf = 1.35 min<br>(column A) |

TABLE C-continued

| Compd. Number | Product's Structure | Method Used | MS (M + H)+ Calcd. | MS (M + H)+ Observ. And Retention Time and NMR |
|---|---|---|---|---|
| AM-05 | | D | 556.17 | 556.21<br>Rf = 1.16 min<br>(column A) |
| AM-06 | | D | 570.15 | 570.16<br>Rf = 1.15 min<br>(column A) |
| AM-07 | | D | 547.07 | 546.94<br>Rf = 1.05 min<br>(column C, solvent system II) |
| AM-08 | | D | 455.19 | 455.18<br>Rf = 1.38 min<br>(column B, solvent system II) |

TABLE C-continued

| Compd. Number | Product's Structure | Method Used | MS (M + H)+ Calcd. | MS (M + H)+ Observ. And Retention Time and NMR |
|---|---|---|---|---|
| AM-09 | | D | 457.13 | 457.37<br>Rf = 1.05 min<br>(column B, solvent system II) |
| AM-10 | | B | 472.16 | 472.18<br>Rf = 2.32 min<br>(column E, gradient time = 3 min)<br>$^1$H NMR (500 MHz, CD$_3$OD)<br>δ 8.79 (d, 1H, J = 10 Hz), 8.36 (d, 1H, J = 10 Hz), 8.13 (ss, 1H), 7.91 (s, 1H), 7.58-7.35 (m, 5H), 4.09-3.52 (m, 8H) |
| AM-11 | | B | 584.22 | 584.21<br>Rf = 2.30 min<br>(column E)<br>$^1$H NMR (500 MHz, CD$_3$OD) δ 8.67 (d, 1H, J = 10 Hz), 8.20 (ss, 1H), 8.16 (m, 2H),<br>7.77 (m, 3H), 7.20-7.25 (m, 5H), 6.95 (b, 1H), 4.10-3.44 (m, 8H), 4.03 (s, 3H) |
| AM-12 | | D | 375.18 | 375.19<br>Rf = 1.06 min<br>(column A) |

TABLE C-continued
| Compd. Number | Product's Structure | Method Used | MS (M + H)+ Calcd. | MS (M + H)+ Observ. And Retention Time and NMR |
|---|---|---|---|---|
| AM-13 | 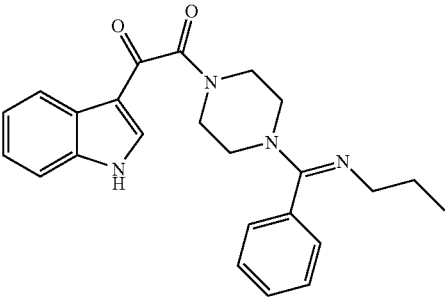 | D | 403.21 | 403.25<br>Rf = 1.24 min<br>(column A) |
| AM-14 | 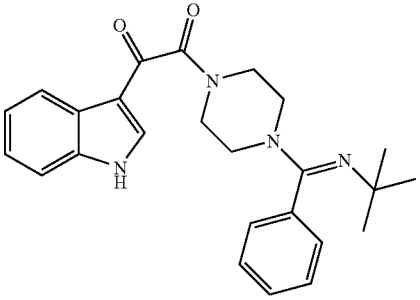 | D | 417.23 | 417.29<br>Rf = 1.26 min<br>(column A) |
| AM-15 | 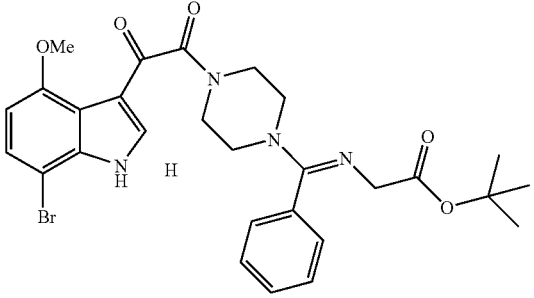 | D | 583.16 | 583.03<br>Rf = 1.30 min<br>(column A) |
| AM-16 | 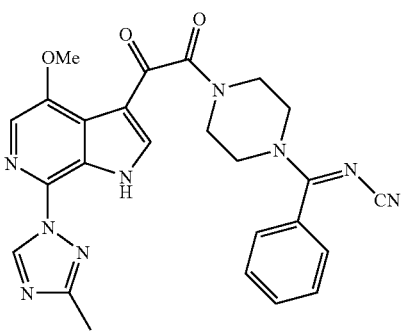 | B | 498.2 | 498.29<br>Rf = 1.00 min<br>(column B, solvent system II)<br>$^1$H NMR (500 MHz, CDCl$_3$)<br>δ 9.74 (ss, 1H), 8.21 (ss, 1H), 7.72 (ss, 1H), 7.55-7.20 (m, 5H), 4.04 (s, 3H), 4.05-3.37 (m, 8H), 2.52 (s, 3H) |

TABLE C-continued

| Compd. Number | Product's Structure | Method Used | MS (M + H)+ Calcd. | MS (M + H)+ Observ. And Retention Time and NMR |
|---|---|---|---|---|
| AM-17 | | D | 482.06 | 482.08<br>Rf = 1.88 min<br>(column F, flow rate = 4 ml/min)<br>$^1$H NMR (500 MHz, CD$_3$OD)<br>δ 8.19 (ss, 1H), 7.61-7.42 (m, 6H), 6.92 (m, 1H), 4.09-3.41 (m, 8H) |
| AM-18 | | A | 393.17 | 393.16<br>Rf = 2.34 min<br>(column G, flow rate = 4 ml/min, gradient time = 3 min) |
| AM-19 | | D | 467.21 | 467.28<br>Rf = 1.80 min<br>(column E) |
| AM-20 | | D | 464.25 | 464.31<br>Rf = 1.62 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-21 | | D | 419.19 | 419.24<br>Rf = 1.91 min<br>(column E) |
| AM-22 | | D | 456.18 | 456.23<br>Rf = 1.87 min<br>(column E) |
| AM-23 | | D | 492.24 | 492.29<br>Rf = 1.62 min<br>(column E) |
| AM-24 | | C | 484.18 | 484.24<br>Rf = 2.08 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-25 | | C | 486.18 | 486.22<br>Rf = 2.19 min<br>(column E)<br>¹H NMR (500 MHz, MeOD) δ ppm 1.20-1.52 (m, 3H), 3.33-4.63 (m, 6H), 4.85-5.07 (m, 1H), 7.26-7.74 (m, 5H), 7.92-7.98 (ss, 1H), 8.10-8.22 (ss, 1H,) 8.33-8.46 (m, 1H), 8.82-8.88 (d, J = 8.24 Hz, 1H) |
| AM-26 | | A | 486.16 | 486.25<br>Rf = 2.11 min<br>(column E) |
| AM-27 | | A | 450.19 | 450.28<br>Rf = 1.99 min<br>(column E) |
| AM-28 | | A | 422.14 | 422.21<br>Rf = 2.08 min<br>(column E)<br>¹H NMR (500 MHz, CDCl₃) δ ppm 3.39-3.72 (m, 5H), 3.87-4.07 (m, 3H), 6.70-6.90 (m, 2H), 7.29-7.57 (m, 5H), 7.84-7.92 (d, J = 9.16 Hz, 1H), 10.34 (s, 1H) |

TABLE C-continued

| Compd. Number | Product's Structure | Method Used | MS (M + H)+ Calcd. | MS (M + H)+ Observ. And Retention Time and NMR |
|---|---|---|---|---|
| AM-29 | | A | 440.15 | 440.20<br>Rf = 1.79 min<br>(column E) |
| AM-30 | | A | 422.14 | 422.20<br>Rf = 2.04 min<br>(column E)<br>¹H NMR (500 MHz, CDCl₃) δ ppm 3.37-3.52 (m, 3H), 3.65-4.08 (m, 5H), 6.80-6.91 (m, 2H), 7.29-7.55 (m, 5H), 7.92-7.98 (d, J = 7.63 Hz, 1H), 10.37 (s, 1H) |
| AM-31 | | A | 440.15 | 440.22<br>Rf = 2.08 min<br>(column E) |
| AM-32 | | A | 422.16 | 422.23<br>Rf = 1.69 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-33 | | B | 461.18 | 461.22<br>Rf = 1.90 min<br>(column E) |
| AM-34 | | B | 459.19 | 459.20<br>Rf = 1.80 min<br>(column E) |
| AM-35 | | C | 437.16 | 459.20<br>Rf = 1.80 min<br>(column E) |
| AM-36 | | C | 464.21 | 464.27<br>Rf = 1.95 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-37 | | C | 549.26 | 549.31<br>Rf = 2.24 min<br>(column E) |
| AM-38 | | C | 480.17 | 480.22<br>Rf = 1.93 min<br>(column E) |
| AM-39 | | C | 508.2 | 508.24<br>Rf = 1.97 min<br>(column E) |
| AM-40 | | C | 522.22 | 522.26<br>Rf = 1.99 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-41 | | C | 665.27 | 665.36<br>Rf = 2.38 min<br>(column E) |
| AM-42 | | C | 536.23 | 538.28<br>Rf = 2.02 min<br>(column E) |
| AM-43 | | C | 693.3 | 693.38<br>Rf = 2.34 min<br>(column E) |
| AM-44 | | C | 563.25 | 564.31<br>Rf = 2.29 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-45 | | C | 749.37 | 749.46<br>Rf = 2.46 min<br>(column E) |
| AM-46 | | C | 498.19 | 498.24<br>Rf = 2.12 min<br>(column E) |
| AM-47 | | C | 562.16 | 562.21<br>Rf = 2.10 min<br>(column E) |
| AM-48 | | C | 745.16 | 745.24<br>Rf = 2.26 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-49 | | C | 542.2 | 542.25<br>Rf = 2.02 min<br>(column E) |
| AM-50 | | C | 624.28 | 624.34<br>Rf = 2.39 min<br>(column E) |
| AM-51 | | C | 521.23 | 521.28<br>Rf = 2.13 min<br>(column E) |
| AM-52 | | C | 447.18 | 447.24<br>Rf = 1.95 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-53 | | B | 512.22 | 512.29<br>Rf = 1.95 min<br>(column E)<br>$^1$H NMR (500 MHz, CD$_3$OD)<br>δ 9.18 (ss, 1H), 8.31 (ss, 1H),<br>7.83 (ss, 1H), 7.66-7.43 (m, 5H),<br>4.00 (s, 3H), 4.10-3.34 (m, 8H),<br>2.90 (q, 2H), J = 10 Hz), 1.39 (t,<br>3H, J = 10 Hz) |
| AM-56 | | D | 501.22 | 501.05<br>Rf = 1.66 min<br>(column F, flow rate = 4 ml/min) |
| AM-58 | | D | 532.26 | 532.38<br>Rf = 1.31 min<br>(column H, flow rate = 4 ml/min) |
| AM-59 | | D | 475.20 | 475.31<br>Rf = 1.47 min<br>(column H, flow rate = 4 ml/min) |

TABLE C-continued

| Compd. Number | Product's Structure | Method Used | MS (M + H)+ Calcd. | MS (M + H)+ Observ. And Retention Time and NMR |
|---|---|---|---|---|
| AM-60 | | D | 535.22 | 535.18<br>Rf = 1.42 min<br>(column F, flow rate = 4 ml/min) |
| AM-61 | | D | 515.23 | 515.19<br>Rf = 1.62 min<br>(column F, flow rate = 4 ml/min) |
| AM-62 | | D | 503.23 | 503.18<br>Rf = 1.65 min<br>(column H, flow rate = 4 ml/min) |
| AM-63 | | D | 529.25 | 529.37<br>Rf = 1.70 min<br>(column E, flow rate = 4 ml/min)<br>$^1$H NMR (500 MHz, MeOD) δ ppm 1.48-1.60 (m, 4H), 1.70-1.92 (m, 6H), 3.33-3.80 (m, 5H), 3.89-4.08 (m, 4H), 7.53-7.79 (m, 3H), 7.99 (s, 1H), 8.16-8.20 (ss, 1H), 8.43 (dd, J = 12.82, 1.83 Hz, 1H), 8.89 (d, J = 10.07 Hz, 1H) |

TABLE C-continued

| Compd. Number | Product's Structure | Method Used | MS (M + H)+ Calcd. | MS (M + H)+ Observ. And Retention Time and NMR |
|---|---|---|---|---|
| AM-64 | | D | 489.22 | 489.35<br>Rf = 1.55 min<br>(column F, flow rate = 4 ml/min)<br>$^1$H NMR (500 MHz, MeOD) δ ppm 1.21-1.25 (m, 6H),<br>3.34-3.48 (m, 3H), 3.62-4.06 (m, 6H), 7.54-7.77 (m, 5H),<br>7.99 (ss, 1H) 8.15-8.19 (ss, 1H)<br>8.42 (d, J = 12.82 Hz, 1H)<br>8.88 (d, J = 9.46 Hz, 1H) |
| AM-65 | | B | 486.18 | 486.19<br>Rf = 2.13 min<br>(column E) |
| AM-66 | | B | 500.20 | 500.22<br>Rf = 2.23 min<br>(column E)<br>$^1$H NMR (500 MHz, CDCl$_3$) δ ppm 0.58-1.10 (m, 3H),<br>1.33-1.84 (m, 2H),<br>2.95-4.08 (m, 5H),<br>4.41-4.98 (m, 2H), 7.16-7.60 (m, 5H), 7.92 (s, 1H), 8.07-8.10 (ss, 1H),<br>8.29-8.43 (m, 1H), 8.71 (d, J = 5.80 Hz, 1H), 11.84 (s, 1H) |
| AM-67 | | B | 554.17 | 554.05<br>Rf = 1.77 min<br>(column F, flow rate = 4 ml/min)<br>$^1$H NMR (300 MHz, MeOD) δ ppm 2.66 (s, 3H), 2.73 (s, 3H),<br>3.24-4.16 (m, 8H), 7.35-7.53 (m, 5H), 7.97 (s, 1H), 8.10-8.15 (ss, 1H), 8.39 (d, J = 5.49 Hz, 1H),<br>8.85 (d, J = 3.29 Hz, 1H) |

TABLE C-continued

| Compd. Number | Product's Structure | Method Used | MS (M + H)+ Calcd. | MS (M + H)+ Observ. And Retention Time and NMR |
|---|---|---|---|---|
| AM-68 | | B | 525.15 | 525.04<br>Rf = 1.69 min<br>(column F, flow rate = 4 ml/min) |
| AM-69 | | B | 461.18 | 461.11<br>Rf = 1.51 min<br>(column F, flow rate = 4 ml/min)<br>$^1$H NMR (300 MHz, MeOD) δ ppm 2.80-2.82 (ss, 3H), 3.51-3.77 (m, 3H), 3.79-4.06 (m, 5H), 7.46-7.71 (m, 5H), 7.98 (d, J = 1.83 Hz, 1H), 8.09-8.20 (m, 1H), 8.44 (d, J = 6.59 Hz, 1H), 8.87 (d, J = 4.76 Hz, 1H) |
| AM-70 | | B | 487.22 | 487.08<br>Rf = 1.89 min<br>(column I)<br>$^1$H NMR (500 MHz, MeOD) δ ppm 2.51-2.52 (ss, 3H), 2.81-2.83 (ss, 3H), 3.52-3.61 (m, 3H), 3.78-3.98 (m, 4H), 4.02 (s, 3H), 4.03-4.08 (m, 1H), 7.51-7.78 (m, 6H), 8.22-8.26 (ss, 1H), 9.15-9.16 (ss, 1H) |
| AM-71 | | B | 484.21 | 483.98<br>Rf = 1.46 min<br>(column E) |

TABLE C-continued

| Compd. Number | Product's Structure | Method Used | MS (M + H)+ Calcd. | MS (M + H)+ Observ. And Retention Time and NMR |
|---|---|---|---|---|
| AM-72 | | B | 484.21 | 483.97<br>Rf = 1.44 min<br>(column E) |
| AM-73 | | A | 457.07 | 457.09<br>Rf = 2.02 min<br>(column I) |
| AM-76 | | A | 496.08 | 496.09<br>Rf = 2.32 min<br>(column I) |
| AM-77 | | E | 462.14 | 462.09<br>Rf = 1.20 min<br>(column I) |

TABLE C-continued
| Compd. Number | Product's Structure | Method Used | MS (M + H)+ Calcd. | MS (M + H)+ Observ. And Retention Time and NMR |
|---|---|---|---|---|
| AM-78 | 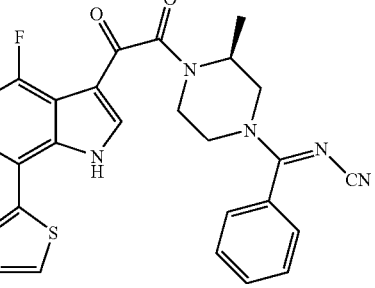 | E | 501.15 | 501.12<br>Rf = 1.45 min<br>(column I) |
| AM-79 | 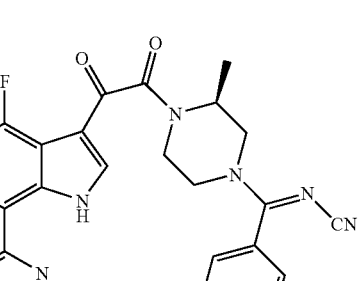 | E | 495.19 | 494.88<br>Rf = 1.75 min<br>(column F, flow rate = 4 ml/min) |
| AM-80 | 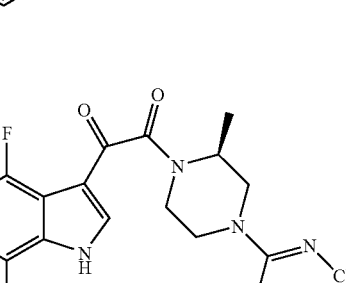 | E | 550.17 | 550.13<br>Rf = 2.24 min<br>(column F, flow rate = 4 ml/min) |
| AM-54 | 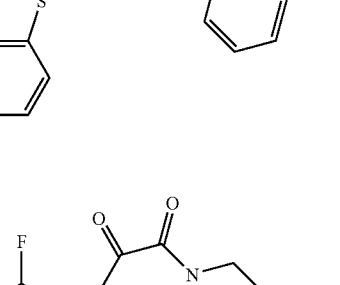 | B | 448.16 | 448.23<br>Rf = 1.91 min<br>(column F, flow rate = 4 ml/min,<br>gradient time = 4 min). |

TABLE C-continued

| Compd. Number | Product's Structure | Method Used | MS (M + H)+ Calcd. | MS (M + H)+ Observ. And Retention Time and NMR |
|---|---|---|---|---|
| AM-55 | | B | 474.20 | 474.10<br>Rf = 1.80 min<br>(column F, flow rate = 4 ml/min, gradient time = 4 min). |
| AM-81 | | C | 473.16 | 473.07<br>Rf = 2.52 min<br>(column F, flow rate = 4 ml/min, gradient time = 4 min). |
| AM-82 | | C | 499.19 | 499.08<br>Rf = 2.37 min<br>(column F, flow rate = 4 ml/min, gradient time = 4 min). |

AM-54: $^1$H NMR (500 MHz, DMSO-d$_6$): δ 9.86 (m, 1 H), 9.61 (m, 1 H), 9.03 (m, 1 H), 8.82 (m, 1 H), 8.46 (br s, 1 H), 8.34 (m, 1 H), 8.20-8.10 (m, 2 H), 7.86 (m, 1 H), 7.74 (m, 1 H), 3.98-3.44 (m, 8 H).

AM-55: $^1$H NMR (500 MHz, DMSO-d$_6$): δ 9.84 (m, 1 H), 9.58 (m, 1 H), 9.26 (m, 1 H), 8.82 (m, 1 H), 8.30 (m, 1 H), 8.15 (m, 1 H), 7.95-7.85 (m, 2 H), 7.74 (m, 1 H), 4.01 (s, 3 H), 3.98-3.42 (m, 8 H), 2.49 (s,3H).

AM-81: $^1$H NMR (500 MHz, DMSO-d$_6$): δ 9.02 (m, 1H), 8.76 (m, 1 H), 8.42 (m, 1 H), 8.32 (m, 1 H), 8.13-8.03 (m, 2 H), 7.73-7.57 (m, 2 H), 4.02-3.87 (m, 2 H), 3.67 (m, 2 H), 3.45 (m, 2 H), 3.28 (m, 2 H).

AM-82: $^1$H NMR (500 MHz, DMSO-d$_6$): δ 9.23 (m, 1 H), 8.76 (m, 1 H), 8.27 (m, 1 H), 8.08 (m, 1 H), 7.90 (m, 1 H), 7.72 (m, 1 H), 7.62 (m, 1 H), 4.00 (s, 3 H), 3.86 (m, 2 H), 3.64 (m, 2 H), 3.42 (m, 2 H), 3.28 (m, 2 H), 2.49 (s, 3 H).

Additional Experimental Procedures:

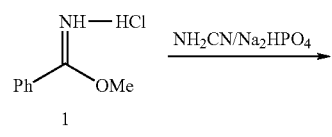

1

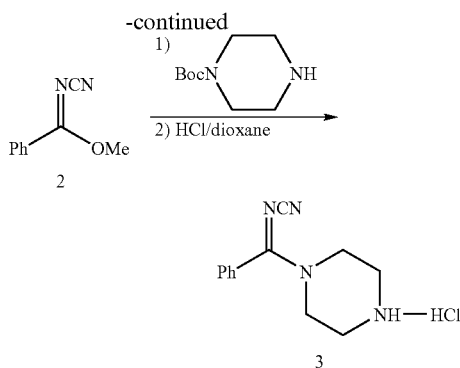

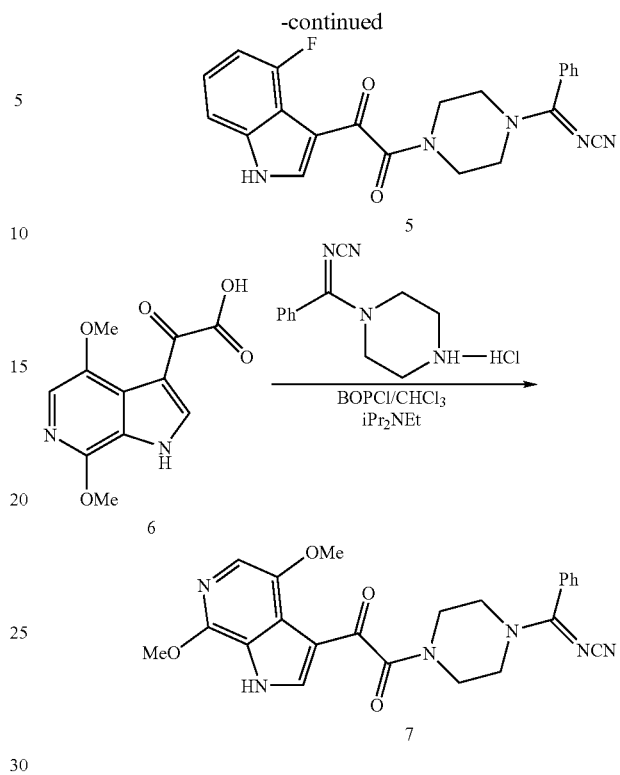

Preparation of N-cyanophenylimidate 2.

A mixture of methyl phenylimidate hydrochloride (7.74 g, 45.1 mmol) and cyanamide (2.66 g, 63.3 mmol) in H$_2$O (5 mL) was cooled to 0° C. and Na$_2$HPO$_4$ (4.60 g, 32.4 mmol) was added. The mixture was allowed to stir 4 h and the liquid decanted from precipitated solids. The remaining solids were partitioned between H$_2$O/Et$_2$O and the layers separated. The aqueous phase was extraced once more with Et$_2$O and the organic layers combined with the decanted liquid. The combined organic phases were washed (H$_2$O, brine) and dried (Na$_2$SO$_4$). The solvents were removed in vacuo and the residual yellow oil was used without further purification. $^1$HNMR (400 MHz, CDCl$_3$) δ 8.06-8.08 (m, 2H), 7.60-7.62 (m, 1H), 7.48-7.53 (m, 2 H), 4.05 (s, 3H). LCMS (m/e) 161 (M$^+$+H). IR (neat) ν$_{max}$=2194.7 cm$^{-1}$.

Preparation of N-cyanoimidate 3.

A mixture of Nbocpiperazine (1.73 g, 9.27 mmol) and N-cyanoimidate 2 (1.55 g, 9.69 mmol) was stirred at rt in MeOH (16 mL) for 4.5 h. The suspension was filtered giving a colorless solid (1.94 g, 64%) which was used as is for subsequent steps.

$^1$HNMR (400 MHz, CDCl$_3$) δ 7.51-7.53 (m, 3H), 7.31-7.35 (m, 2H), 3.87 (t, J=2.8 Hz, 2H), 3.55 (t, J=2.8 Hz, 2H), 3.38 (t, J=2.8 Hz, 2H), 3.29 (t, J=2.8 Hz, 2H), 1.45 (s, 9H). HPLC t$_r$=1.59 min (Primesphere C-18 HC 4.6×30, 5 mM NH$_4$OAc, CH$_3$CN/H$_2$O). To the imidate 3 (1.00 g, 3.19 mmol) was added HCl (6.0 mL, 4 M in dioxane) at 0° C. After 5 min at 0° C. the ice bath was removed and and the solution allowed to stir at rt for 4 h. The solvent was removed in vacuo to give a fluffy white solid (785 mg, 98%). $^1$HNMR (400 MHz, MeOD) δ 7.26 (m, 3H), 7.15-7.13 (m, 2H) 3.83 (t, J=5.5 Hz, 2H), 3.27 (m, br, 2H), 3.07 (t, J=5.5 Hz, 2H), 2.95-2.90 (m, 4H). LCMS (m/z) 215 (M$^+$+H).

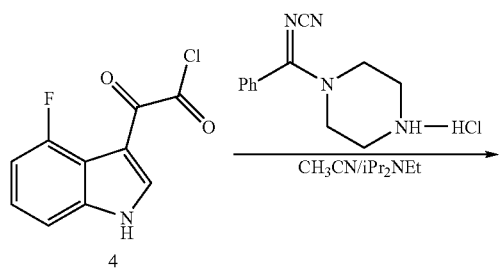

Preparation of Cyanoimidate 5.

To a suspension of acid chloride 4 (50.4 mg, 0.223 mmol), and amine hydrochloride (54.2 mg, 0.216 mmol) in CH$_3$CN (5 mL) was added iPrNEt$_2$ (0.10 mL, 0.574 mmol) and the mixture allowed to stir overnight at rt. The mixture was filtered to remove excess starting amine hydrochloride and the solvent removed in vacuo. The residue was purified by preparative HPLC giving 5 as a yellow wax (12.8 mg, 15%).

$^1$H NMR (400 MHz, DMSO-d6) δ 9.80 (s, 1H), 7.95 (dd, J=11.8, 3.1 Hz, 1H), 7.55-7.49 (m, 3H), 7.38-7.30 (m, 2H), 7.20-7.15 (m, 2H), 6.99-6.94 (m, 1H), 4.05 (dd app t, J=5.3, 4.8 Hz, 1H), 3.97 (dd app t, J=5.3, 4.8 Hz, 1H), 3.91 (dd app t, J=5.3, 4.8 Hz, 1H), 3.70-3.50 (m, 2H), 3.49-3.45 (m, 2H), (dd app t, J=5.3, 4.8 Hz, 1H). LCMS: m/e 404 (M+H)$^+$.

Preparation of Cyanoimidate 7:

To a solution of 4,7-dimethoxy-6-azaindoleoxoacetic acid hydrate (6), (48.0 mg, 0.179 mmol) and iPr$_2$NEt (0.07 mL, 0.402 mmol) in CHCl$_3$ (4 mL) was added BOPCl (45.6 mg, 0.179 mmol). The mixture was allowed to stir at rt for 6 h and the solvent was removed in vacuo. The residue was partitioned between H$_2$O and EtOAc and the layers separated. The aqueous phase was extracted twice more with EtOAc and the combined organic layers were washed (H$_2$O, brine) and dried (Na$_2$SO$_4$). The solvent was removed in vacuo and the residue was purified by preparative HPLC to give 7 as a colorless solid (14.6 mg, 18%). The $^1$H NMR showed a 1:1 mixture of rotamers. $^1$HNMR (400 MHz, DMSO-d$_6$) δ 8.16, 8.13 (d, J=3.3 Hz, 1H), 7.60-7.58 (m, 2H), 7.55-7.52 (m, 1H), 7.50-7.43 (m, 3H), 3.98, 3.96 (s, 3H), 3.96-3.93 (m, br, 2H) 3.83, 3.82 (s, 3H), 3.80-3.75 (m, br, 2H), 3.63-3.60 (m, 1H), 3.52-3.60 (m, 1H), 3.39-3.36 (m, 1H), 3.25-3.22 (m, 1H).

LCMS: m/e 447 (M+H)$^+$.

Biology

"μM" means micromolar;

"mL" means milliliter;

"μl" means microliter;
"mg" means milligram;

The materials and experimental procedures used to obtain the results reported in Tables 1-2 are described below.

Cells

Virus production—Human embryonic Kidney cell line, 293T, was propagated in Dulbecco's Modified Eagle Medium (Invitrogen, Carlsbad, Calif.) containing 10% fetal Bovine serum (FBS, Sigma, St. Louis, Mo.).

Virus infection—Human epithelial cell line, HeLa, expressing the HIV-1 receptor CD4 was propagated in Dulbecco's Modified Eagle Medium (Invitrogen, Carlsbad, Calif.) containing 10% fetal Bovine serum (FBS, Sigma, St. Louis , Mo.) and supplemented with 0.2 mg/mL Geneticin (Invitrogen, Carlsbad, Calif.). Virus-Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Invitrogen, Carlsbad, Calif.).

Experiment

1. HeLa CD4 cells were plated in 96 well plates at a cell density of $1 \times 10^4$ cells per well in 100 μl Dulbecco's Modified Eagle Medium containing 10% fetal Bovine serum and incubated overnight.
2. Compound was added in a 2 μl dimethylsulfoxide solution, so that the final assay concentration would be $\leq 10$ μM.
3. 100 μl of single-round infectious reporter virus in Dulbecco's Modified Eagle Medium was then added to the plated cells and compound at an approximate multiplicity of infection (MOI) of 0.01, resulting in a final volume of 200 μl per well.
4. Virally-infected cells were incubated at 37 degrees Celsius, in a $CO_2$ incubator, and harvested 72 h after infection.
5. Viral infection was monitored by measuring luciferase expression from viral DNA in the infected cells using a luciferase reporter gene assay kit, as described by the manufacturer (Roche Molecular Biochemicals, Indianapolis, Ind.). Infected cell supernatants were removed and 50 μl of lysis buffer was added per well. After 15 minutes, 50 μl of freshly-reconstituted luciferase assay reagent was added per well. Luciferase activity was then quantified by measuring luminescence using a Wallac microbeta scintillation counter.
6. The percent inhibition for each compound was calculated by quantifying the level of luciferase expression in cells infected in the presence of each compound as a percentage of that observed for cells infected in the absence of compound and subtracting such a determined value from 100.
7. An $EC_{50}$ provides a method for comparing the antiviral potency of the compounds of this disclosure. The effective concentration for fifty percent inhibition ($EC_{50}$) was calculated with the Microsoft Excel Xlfit curve fitting software. For each compound, curves were generated from percent inhibition calculated at 10 different concentrations by using a four paramenter logistic model (model 205). The $EC_{50}$ data for the compounds is shown in Table 2. Table 1 is the key for the data in Table 2.

Results

TABLE 1

Biological Data Key for $EC_{50}s$

| Compounds with $EC_{50}s > 0.5$ μM | Compounds with $EC_{50} < 0.5$ μM |
|---|---|
| Group B | Group A |

TABLE 2

| Compd. Number | Structure | $EC_{50}$ Group from Table 1 |
|---|---|---|
| AM-01 | 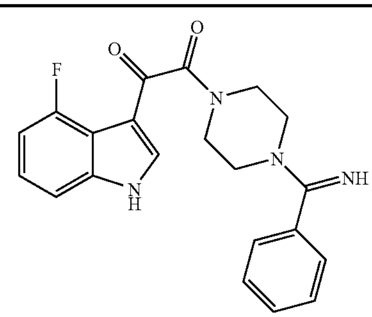 | A |
| AM-02 | 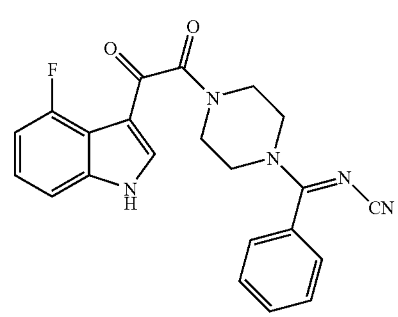 | A |

TABLE 2-continued

| Compd. Number | Structure | EC$_{50}$ Group from Table 1 |
|---|---|---|
| AM-03 | 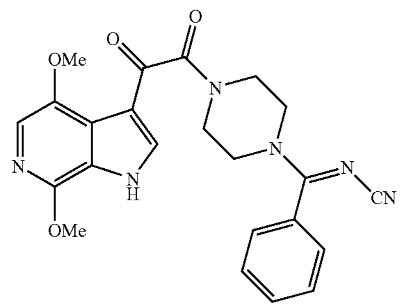 | A |
| AM-04 | 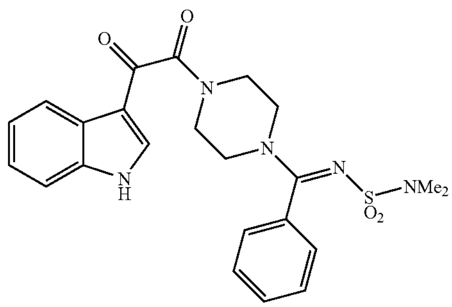 | A |
| AM-05 | 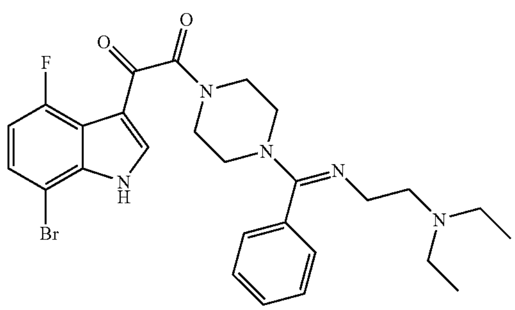 | A |
| AM-06 | 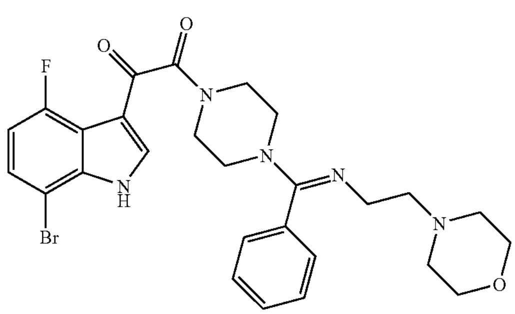 | A |
| AM-07 | 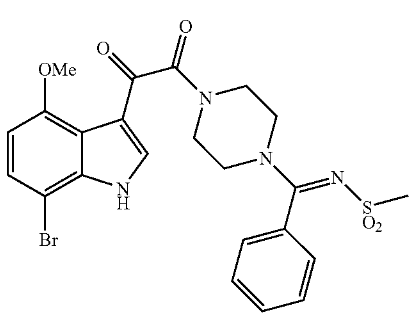 | A |

TABLE 2-continued

| Compd. Number | Structure | EC$_{50}$ Group from Table 1 |
|---|---|---|
| AM-08 | 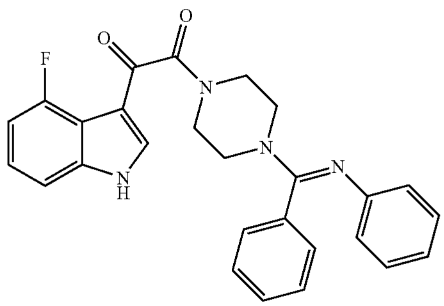 | A |
| AM-09 | 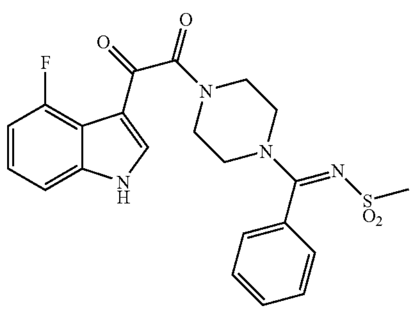 | A |
| AM-10 | 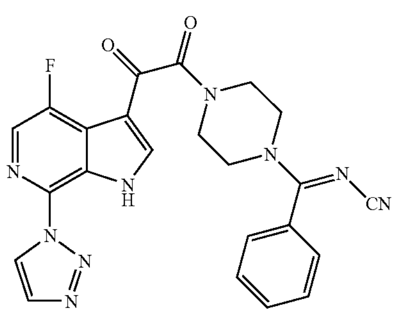 | A |
| AM-11 | 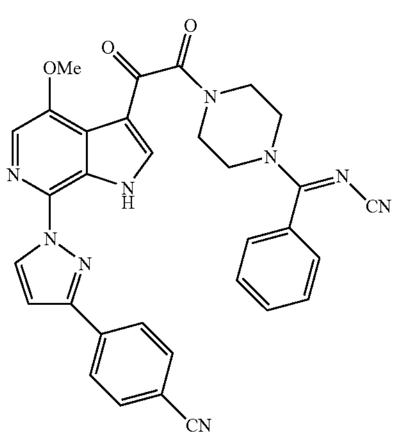 | A |

TABLE 2-continued
| Compd. Number | Structure | EC$_{50}$ Group from Table 1 |
|---|---|---|
| AM-12 | 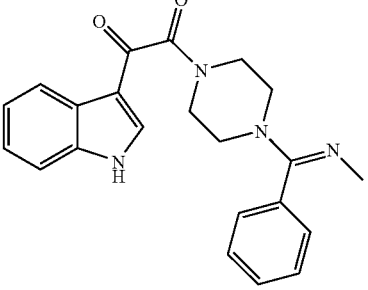 | B |
| AM-13 | 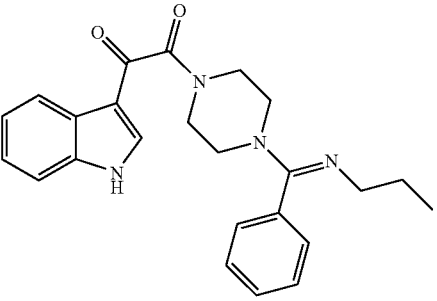 | B |
| AM-14 | 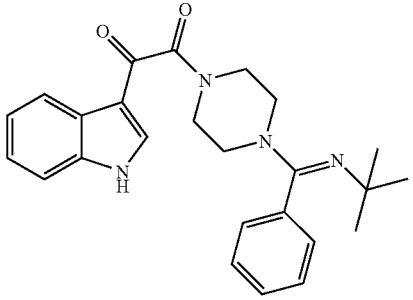 | B |
| AM-16 | 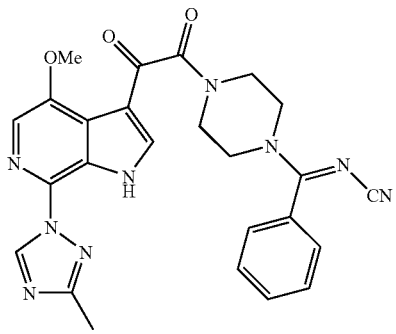 | A |
| AM-17 | 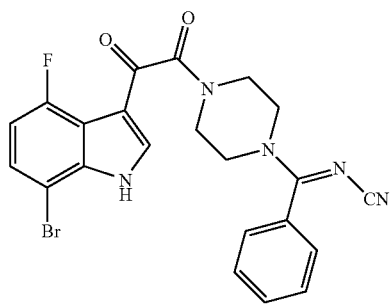 | A |

TABLE 2-continued

| Compd. Number | Structure | EC$_{50}$ Group from Table 1 |
|---|---|---|
| AM-18 | 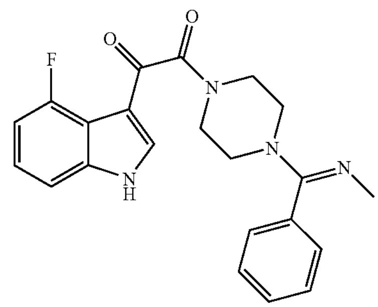 | B |
| AM-19 | 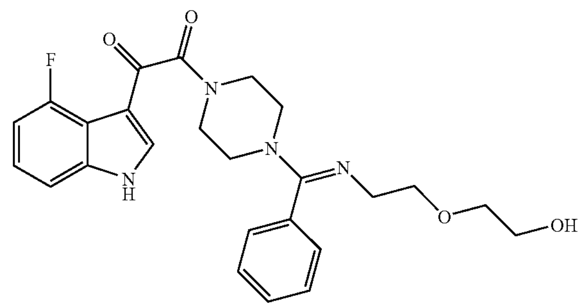 | B |
| AM-20 | 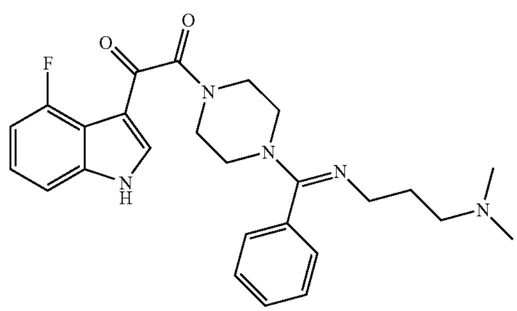 | B |
| AM-21 | 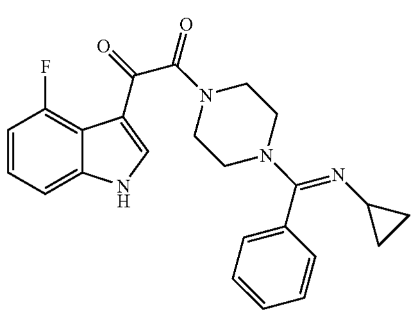 | B |
| AM-22 | 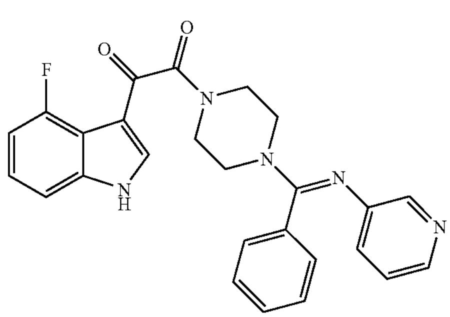 | B |

TABLE 2-continued

| Compd. Number | Structure | EC$_{50}$ Group from Table 1 |
|---|---|---|
| AM-23 | 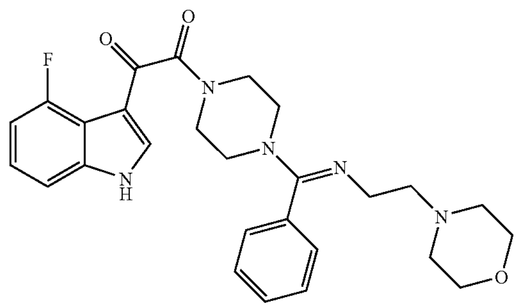 | B |
| AM-24 | 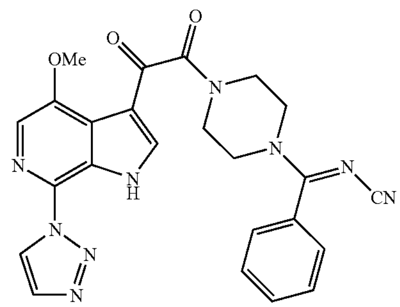 | A |
| AM-25 | 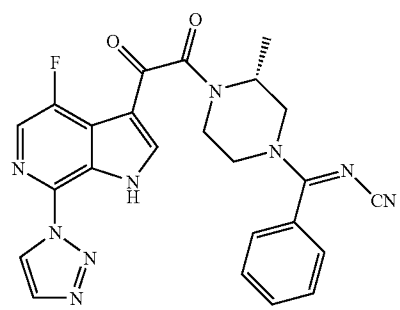 | A |
| AM-26 | 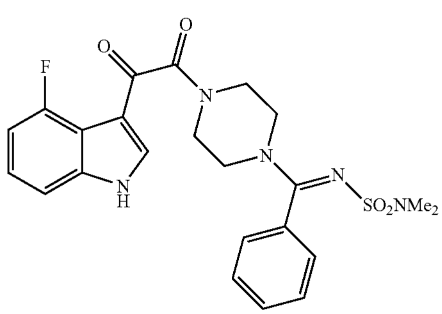 | B |
| AM-28 | 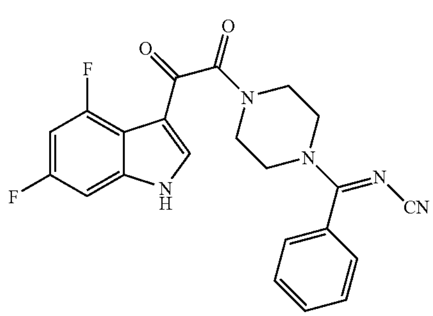 | A |

TABLE 2-continued
| Compd. Number | Structure | EC$_{50}$ Group from Table 1 |
|---|---|---|
| AM-30 | 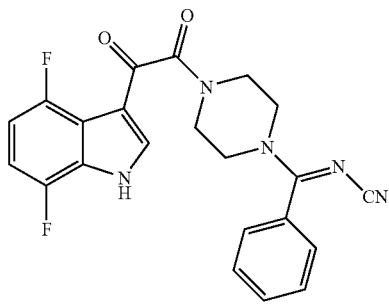 | A |
| AM-33 | 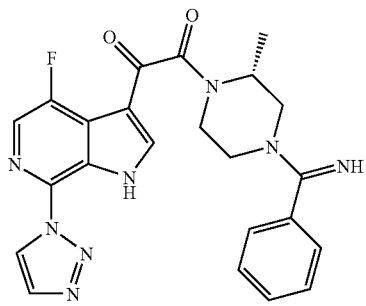 | A |
| AM-34 | 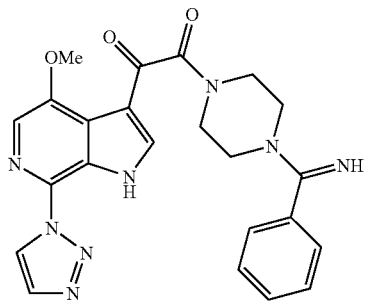 | A |
| AM-36 | 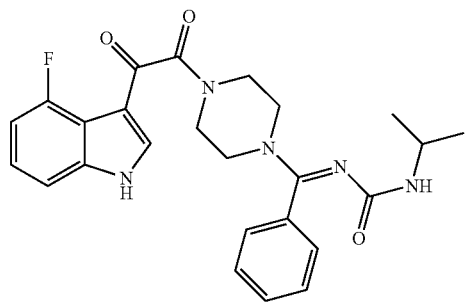 | B |

TABLE 2-continued

| Compd. Number | Structure | EC$_{50}$ Group from Table 1 |
|---|---|---|
| AM-50 | 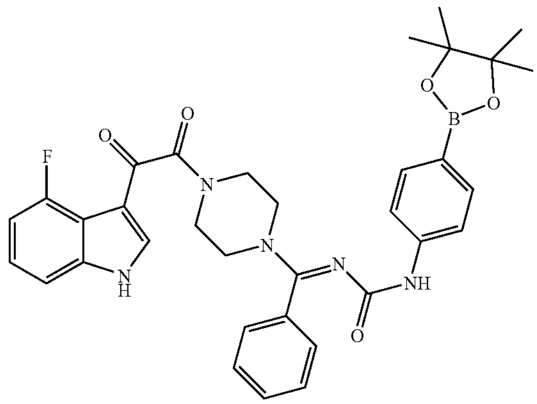 | B |
| AM-53 | 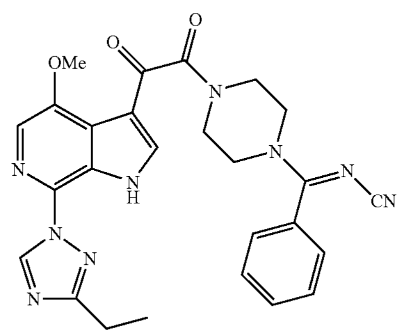 | A |
| AM-56 | 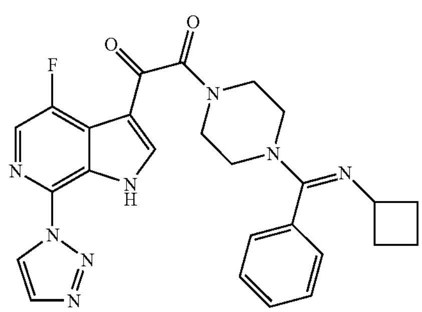 | A |
| AM-58 | 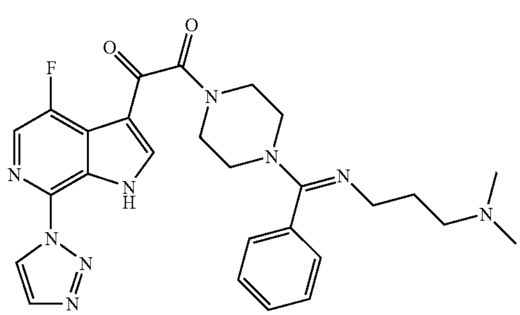 | A |

TABLE 2-continued
| Compd. Number | Structure | EC$_{50}$ Group from Table 1 |
|---|---|---|
| AM-59 | 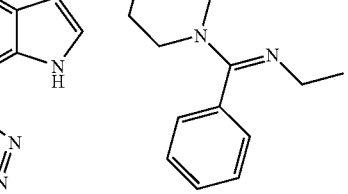 | A |
| AM-60 | 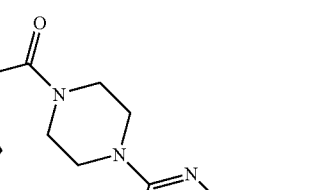 | A |
| AM-61 | 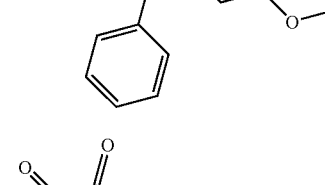 | A |
| AM-62 | 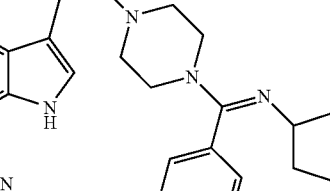 | A |
| AM-63 | 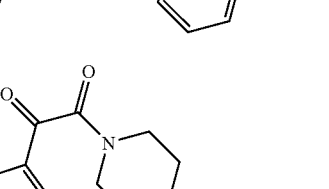 | A |

TABLE 2-continued

| Compd. Number | Structure | EC$_{50}$ Group from Table 1 |
|---|---|---|
| AM-64 | 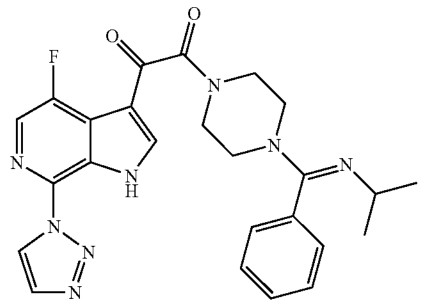 | A |
| AM-65 | 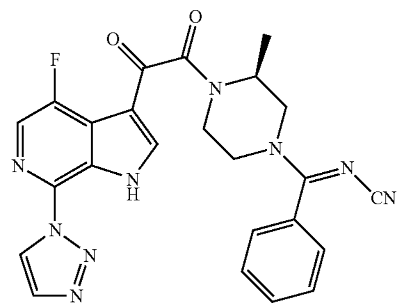 | A |
| AM-66 | 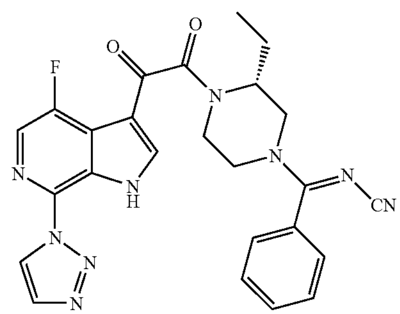 | A |
| AM-67 | 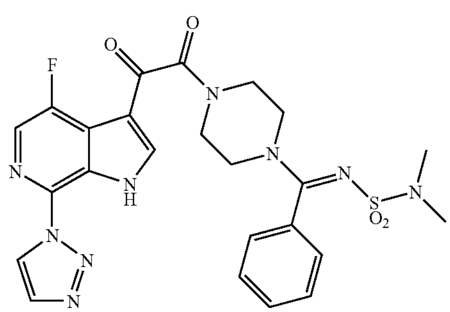 | A |
| AM-68 | 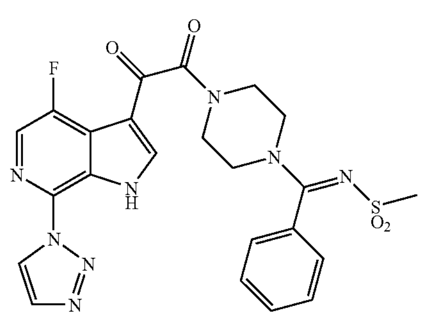 | A |

TABLE 2-continued
| Compd. Number | Structure | EC$_{50}$ Group from Table 1 |
|---|---|---|
| AM-69 | 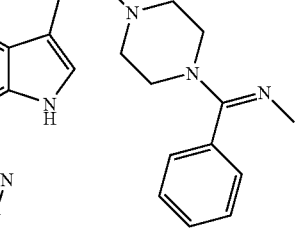 | A |
| AM-70 | 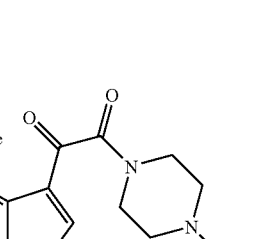 | A |
| AM-71 | 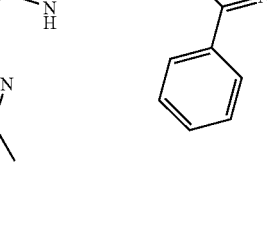 | A |
| AM-72 | 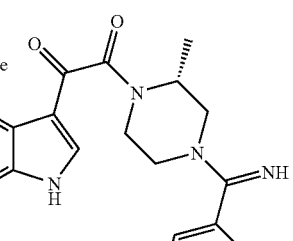 | A |

TABLE 2-continued

| Compd. Number | Structure | EC$_{50}$ Group from Table 1 |
|---|---|---|
| AM-73 | 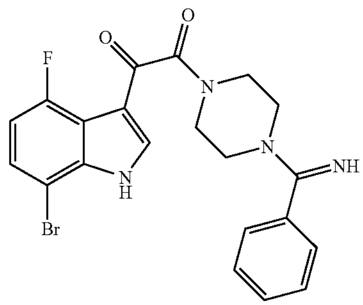 | A |
| AM-76 | 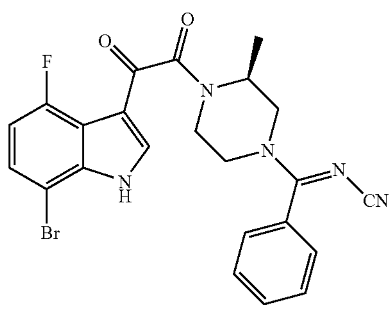 | A |
| AM-77 | 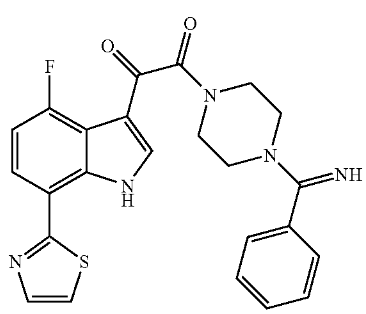 | A |
| AM-78 | 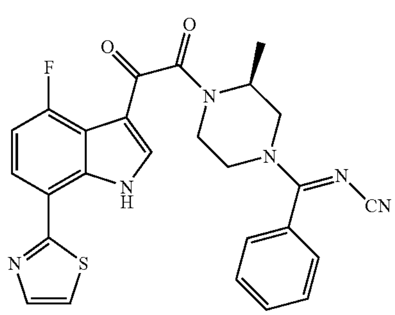 | A |
| AM-79 | 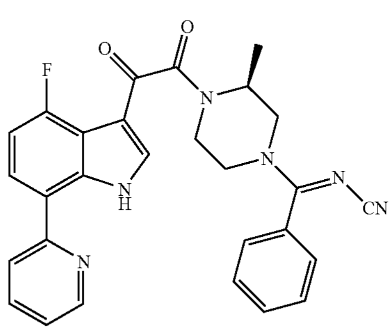 | A |

TABLE 2-continued
| Compd. Number | Structure | EC$_{50}$ Group from Table 1 |
|---|---|---|
| AM-80 | 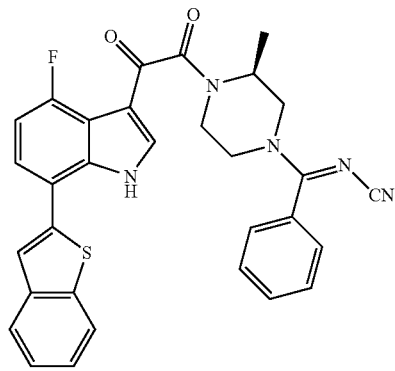 | A |
| AM-54 | 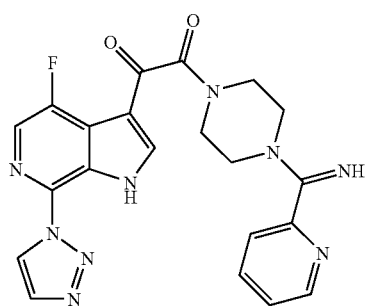 | A |
| AM-55 | 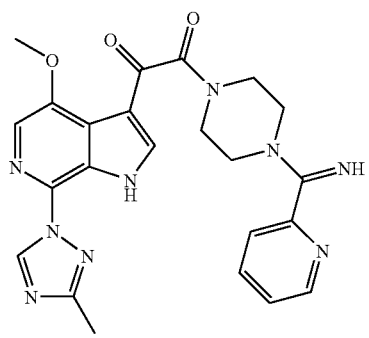 | A |
| AM-81 | 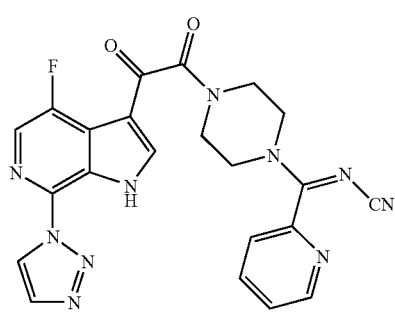 | A |

TABLE 2-continued

| Compd. Number | Structure | EC$_{50}$ Group from Table 1 |
|---|---|---|
| AM-82 | 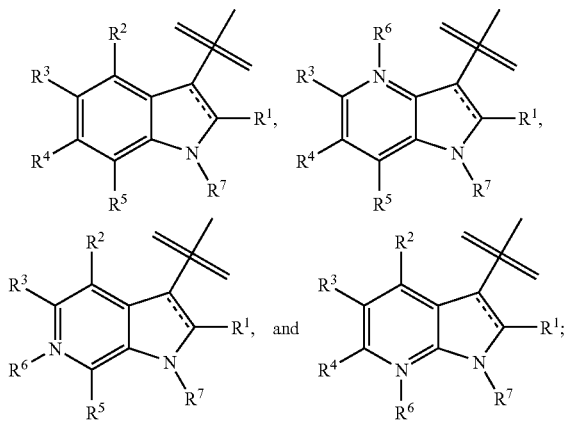 | A |

The compounds of the present disclosure may be administered orally, parenterally (including subcutaneous injections, intravenous, intramuscular, intrasternal injection or infusion techniques), by inhalation spray, or rectally, in dosage unit formulations containing conventional non-toxic pharmaceutically acceptable carriers, adjuvants and diluents.

Thus, in accordance with the present disclosure, there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically effective amount of a compound of the present disclosure.

The pharmaceutical composition may be in the form of orally administrable suspensions or tablets; nasal sprays, sterile injectable preparations, for example, as sterile injectable aqueous or oleagenous suspensions or suppositories.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this disclosure can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

What is claimed is:
1. A compound of Formula I, or a pharmaceutically acceptable salt thereof,

wherein:
X is selected from the group consisting of:

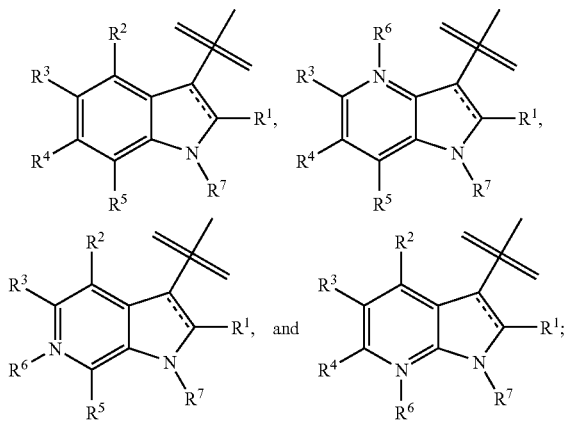

$R^1$ is H;
$R^2$ is halogen or $C_1$-$C_3$ alkoxy;
$R^3$ and $R^4$ are independently H or halogen;
$R^5$ is selected from the group consisting of hydrogen, halogen, methoxy, and B;
$R^6$ is O or does not exist;
═══represents a carbon-carbon bond;
B is selected from the group consisting of $C(O)NR^{14}R^{15}$, phenyl and heteroaryl; wherein said phenyl and heteroaryl are independently optionally substituted with one to three same or different halogens or from one to three same or different substituents selected from F defined below; heteroaryl is selected from the group consisting of pyridinyl, pyrazinyl, pyridazinyl, pyrimidinyl, furanyl, thienyl, thiazolyl, imidazolyl, oxadiazolyl, thiadiazolyl, pyrazolyl, tetrazolyl, and triazolyl;

F is selected from the group consisting of $(C_{1-6})$alkyl, phenyl, and —$CONR^{16}R^{17}$; wherein said phenyl is optionally substituted with one to three same or different halogens or one to three methyl groups or cyano;

$R^{14}$ and $R^{15}$ are independently hydrogen or $C_{1-6}$alkyl;

$R^{16}$ and $R^{17}$ are independently hydrogen or $(C_{1-6})$alkyl;

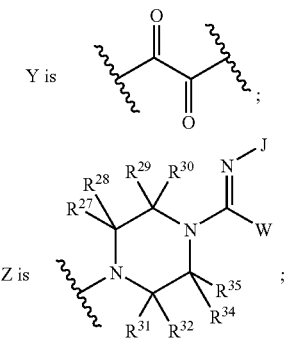

J is selected from the group consisting of hydrogen, $(C_{1-6})$ alkyl, phenyl, pyridyl, $(C_{3-6})$cycloalkyl, $C(=O)NR^{18}R^{19}$, $C(=O)OR^{20}$, $C(=O)R^{21}$, cyano, and $SO_2G^3$, wherein said $(C_{1-6})$alkyl, may be optionally substituted with one to three same or different members selected from the group J-1;

$R^{18}$ and $R^{19}$ are each independently H, $(C_{1-6})$alkyl, or phenyl;

$R^{20}$ and $R^{21}$ are each independently $(C_{1-6})$alkyl;

$G^3$ is selected from the group consisting of $(C_{1-6})$alkyl, $(C_{3-6})$ cycloalkyl, $N((C_{1-6})alkyl)_2$, and phenyl;

J-1 is selected from the group consisting of —$N(CH_3)_2$, morpholino, piperazinyl, hydroxy, alkyloxy, and N-Me piperazinyl;

W is phenyl or pyridinyl;

$R^{27}$, $R^{28}$, $R^{29}$, $R^{30}$, $R^{31}$, $R^{32}$, $R^{34}$ and $R^{35}$ are independently selected from the group consisting of hydrogen, or one or two $(C_{1-6})$alkyl optionally substituted with 1 to 3 fluorines.

2. The compound of claim 1 wherein J is $CH_3$, CN, or H.

3. A pharmaceutical composition which comprises an antiviral effective amount of a compound of Formula I, or a pharmaceutically acceptable salt thereof, as claimed in claim 1, and one or more pharmaceutically acceptable carriers, excipients or diluents.

4. The pharmaceutical composition of claim 3, useful for treating infection by HIV, which additionally comprises an antiviral effective amount of an AIDS treatment agent selected from the group consisting of:
 (a) an AIDS antiviral agent;
 (b) an anti-infective agent;
 (c) an immunomodulator; and
 (d) HIV entry inhibitors.

5. A method for treating a mammal infected with an HIV virus comprising administering to said mammal an antiviral effective amount of a compound of Formula I, or a pharmaceutically acceptable salt thereof, as claimed in claim 1, and one or more pharmaceutically acceptable carriers, excipients or diluents.

6. The method of claim 5, comprising administering to said mammal an antiviral effective amount of a compound of Formula I in combination with an antiviral effective amount of an AIDS treatment agent selected from the group consisting of: an AIDS antiviral agent; an anti-infective agent; an immunomodulator; and an HIV entry inhibitor.

* * * * *